(12) United States Patent
Chung et al.

(10) Patent No.: US 9,012,606 B2
(45) Date of Patent: Apr. 21, 2015

(54) IN VIVO HALF LIFE INCREASED FUSION PROTEIN OR PEPTIDE MAINTAINED BY SUSTAINED IN VIVO RELEASE, AND METHOD FOR INCREASNG IN VIVO HALF-LIFE USING SAME

(75) Inventors: Hye-Shin Chung, Daejeon (KR); Seung Bum Yoo, Daejeon (KR); Sang Mee Lee, Daejeon (KR)

(73) Assignee: Alteogen, Inc., Daejeon (KR)

( * ) Notice: Subject to any disclaimer, the term of this patent is extended or adjusted under 35 U.S.C. 154(b) by 541 days.

(21) Appl. No.: 13/265,775

(22) PCT Filed: Apr. 22, 2010

(86) PCT No.: PCT/KR2010/002520
§ 371 (c)(1),
(2), (4) Date: Oct. 21, 2011

(87) PCT Pub. No.: WO2010/123290
PCT Pub. Date: Oct. 28, 2010

(65) Prior Publication Data
US 2012/0094356 A1    Apr. 19, 2012

(30) Foreign Application Priority Data

Apr. 22, 2009    (KR) .................. 10-2009-0035190

(51) Int. Cl.
*C07K 1/00* (2006.01)
*C07K 14/81* (2006.01)

(52) U.S. Cl.
CPC ......... *C07K 14/8125* (2013.01); *C07K 2319/31* (2013.01)

(58) Field of Classification Search
USPC ....................................................... 530/350
See application file for complete search history.

(56) References Cited

U.S. PATENT DOCUMENTS

| 7,247,704 | B2 | 7/2007 | Barr et al. | |
| 2005/0084972 | A1* | 4/2005 | Barr et al. | 435/483 |
| 2008/0260757 | A1 | 10/2008 | Holt et al. | |

FOREIGN PATENT DOCUMENTS

WO    2009/018441    2/2009

OTHER PUBLICATIONS

Japanese Office Action—2012-505833.
Bernard Vanhove, et al., "Selective Blockade of CD28 and not CTLA-4 With a Single-Chain . . ." Immunobiology, Blood, Jul. 15, 2003, vol. 102, No. 2 564-570.
Mohammad Hashemi, et al., "Impaired Activity of Serum Alpha-1-Antitrypsin in Diabetes Mellitus"; Science Direct, 246-248, 75, 2007.
Steven W. Griffiths, et al., "Development of a Peptide Mapping Procedure to Identify and Quantify Methionine Oxidation . . .", Journal of Chromatography A., 942 (2002) 133-143.
VanHove B. et al., "Selective blockade of CD28 and not CTLA-4 with a single claim Fv-α1-antitrypsin fusion antibody" Blood. vol. 102, pp. 564-570. Mar. 20, 2003.
Hashemi M. et al., "Impaired activity of serum alpha-1-antitrypsin in diabetes mellitus" Diabetes Research and Clinical Practice. vol. 75, pp. 246-248. Jul. 27, 2006.
Jazayeri J.A. and Carroll G.J., "Fc-based cytokines" Biodrugs. vol. 22, pp. 11-26 Jan. 1, 2008.
Krippner-Heidenreich A. et al., "Single-chain TNF, a TNF derivative with enhanced stability and antitumoral activity" The Journal of Immunology. vol. 180, pp. 8176-8183, Jun. 15, 2008.
Steven W. Griffiths, et al., Development of a Peptide Mapping Procedure to Identify and Quantify . . . Journal of Chrom. A., vol. 942, pp. 133-143, 2002.
Shi-Da Yu, et al., The Role of Sialic Acid and Galactose . . . , Archives of Biochemistry and Biophysics, vol. 179, pp. 477-485, 1977.
Nancy Matheson, et al., The Promary Role of the p1 . . . , pp. 271-277, 1989.
James k. Stoller, x1-antitrypsin deficiency, www.thelancet.com, vol. 365, 2005.
Philip A. Patston, et al., Reactivity of x1-Antitrypsin Mutants . . . , The Journal of Biological Chemistry, vol. 265, No. 18, Issue of June, pp. 10786-10791, 1990.

* cited by examiner

*Primary Examiner* — Maryam Monshipouri
(74) *Attorney, Agent, or Firm* — Lucas & Mercanti, LLP

(57) ABSTRACT

The present invention relates to a fusion protein or peptide, the in vivo half-life of which is increased by maintaining in vivo sustained release, and to a method for increasing in vivo half-life using same. A fusion protein or peptide according to the present invention has excellent in vivo stability by binding a physiologically active protein or physiologically active peptide to an alpha-1 antitrypsin or alpha-1 antitrypsin mutant with one or more amino acids mutated to maintain the in vivo sustained release and to significantly increase the half-life thereof in blood (T1/2) compared to an inherent physiologically active protein or physiologically active peptide. Thus, a fusion protein or peptide according to the present invention can be useful in developing a sustained-release preparation of a protein or peptide drug.

5 Claims, 13 Drawing Sheets hGH : human growth hormone

T109wt : human growth hormone/alpha-1 antitrypsin fusion

T109 : human growth hormone/alpha-1 antitrypsin monovariant fusion

T109T : human growth hormone/alpha-1 antitrypsin divariant fusion

IFN-α : human interferon alpha

T502 : human interferon alpha/alpha-1 antitrypsin monovariant fusion

Filgrastim : G-CSF (granulocyte colony-stimulating factor)

T602S : granulocyte colony-stimulating factor/alpha-1 antitrypsin divariant fusion T602ST : granulocyte colony-stimulating factor/alpha-1 antitrypsin trivariant fusion Exendin-4 : exendin-4

T304 : exendin-4/alpha-1 antitrypsin monovariant fusion hGH : human growth hormone T109 : human growth hormone/alpha-1 antitrypsin monovariant fusion PBS : phosphate buffered saline Filgrastim : granulocyte colony-stimulating factor T602S : granulocyte colony-stimulating factor/alpha-1 antitrypsin divariant fusion T602ST : granulocyte colony-stimulating factor/alpha-1 antitrypsin trivariant fusion PBS: phosphate buffered saline
Exendin-4 : exendin-4
T304 : exendin-4/alpha-1 antitrypsin monovariant fusion PBS: phosphate buffered saline
Exenatide: exendin-4
T304: exendin-4/alpha-1 antitrypsin monovariant fusion T109wt : human growth hormone/alpha-1 antitrypsin fusion T109 : human growth hormone/alpha-1 antitrypsin monovariant fusion T109T : human growth hormone/alpha-1 antitrypsin divariant fusion T602S : granulocyte colony-stimulating factor/alpha-1 antitrypsin divariant fusion T602ST : granulocyte colony-stimulating factor/alpha-1 antitrypsin trivariant fusion T109wt : human growth hormone/alpha-1 antitrypsin fusion T109 : human growth hormone/alpha-1 antitrypsin monovariant fusion T109wt : human growth hormone/alpha-1 antitrypsin fusion T109 : human growth hormone/alpha-1 antitrypsin monovariant fusion M: molecular weight marker
1: human growth hormone/alpha-1 antitrypsin fusion (T109wt)
2: human growth hormone/alpha-1 antitrypsin monovariant fusion (T109)
3: human growth hormone/alpha-1 antitrypsin divariant fusion (T109T)

IN VIVO HALF LIFE INCREASED FUSION PROTEIN OR PEPTIDE MAINTAINED BY SUSTAINED IN VIVO RELEASE, AND METHOD FOR INCREASNG IN VIVO HALF-LIFE USING SAME

CROSS-REFERENCE TO RELATED APPLICATIONS

This application is a 371 of PCT/KR2010/002520 filed on Apr. 22, 2010, which claims the benefit of Korean Patent Application No. 10-2009-0035190 filed Apr. 22, 2009, the contents of each of which are incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 23, 2011 is named Sequence-US and is 36,864 bytes in size.

TECHNICAL FIELD

The present invention relates to a fusion protein or peptide having increased in vivo half-life, and a method for increasing in vivo half-life of a protein or peptide using the same.

BACKGROUND ART

Protein and peptide drugs have excellent therapeutic effects that otherwise cannot be treated by general synthetic chemical drugs, and thus take important positions in medicine and pharmacy. For example, recombinant human growth hormone (hGH) is the sole effective therapeutic agent for the treatment of growth hormone deficiency, and recombinant human erythropoietin (EPO) is used in treating anemia resulting from chronic kidney disease due to its ability to increase the level of red blood cells, and recombinant granulocyte colony stimulating hormone (G-CSF) is used as the sole drug to increase the white blood cell count in cancer patients after chemotherapy. In addition, various kinds of cytokines, hormones and peptides which are found in the body are used as the sole therapeutics for a wide spectrum of diseases for which no other alternatives are currently available.

Although they exhibit excellent therapeutic effects in vivo, these protein or peptide drugs quickly lose their therapeutic activity and thus have short half-lives in vivo because they are degraded by blood proteinases immediately after injection or they are readily removed from the body by the kidney or liver. Thus, they are disadvantageous in that they require frequent injections in order to maintain a constant blood level or titer thereof. Such frequent injection lowers the drug compliance of patients because of the fear and pain of injection or inconvenience by repeated administrations when they are used for a long period of time.

Many studies have been continuously conducted in order to increase the blood stability of protein and peptide drugs and maintain the levels of the drugs in the blood for a long period of time.

For example, sustained release dosage forms of drugs have been developed by formulating a therapeutically active protein or peptide with a bio-degradable polymer that allows proteins or peptides to be slowly released from the injection site. When the sustained release drug is subcutaneously or intramuscularly injected, the drug is slowly released to maintain the drug at a constant level for a specific period of time (M. Chasin & R. Langer, et al., Biodegradable polymer as drug delivery system, Marcel Dekker (1990); J. Heller, et al., *Adv. Drug Del Rev.*, 10, 163 (1993)). Among the bio-degradable polymers, PLGA (poly(lactic-co-glycolic acid) has been widely used. For example, a sustained dosage form of LHRH (luteinizing hormone-releasing hormone) agonist peptide was produced, and it was found that this product releases the peptide in vivo over one or three months. The use of biodegradable polymers has been applied to large-molecular weight proteins. For example, U.S. Pat. No. 6,500,448 discloses a pharmaceutical composition for the sustained release of human growth hormone which comprises a biocompatible polymer, and particles of metal cation-complexed human growth hormone. In another study, Korean Patent Nos. 10-0236771 and 10-0329336 described the use of hyaluronic acid for the sustained release microparticles of the protein drugs, featuring the application of recombinant human growth hormone.

Even though, for the sustained release of drugs, bio-degradable polymers have been successfully applied to low-molecular weight peptides, there are limitations concerning their application to large-molecular weight proteins. The reason for this is that proteins are easily denatured in the course of producing sustained release microparticles and the denatured amino acids lower the activity of the protein, which cause some undesired immune responses in human body. In addition, the size of microparticles for the sustained release of proteins or peptides is generally large, requiring thick syringe needles when injected into human, which create pain at injection site. Also, the microparticles have the economical disadvantage of low production yields in the production of the products for the commercial purpose.

In order to overcome the aforementioned problems, studies have been directed towards the delay of renal clearance of proteins or peptides. On the whole, proteins with a molecular weight of 60,000 daltons or less pass through the kidney without renal retention. Hence, attempts have been made to enlarge the low-molecular weight of peptide or protein therapeutics to prolong in vivo circulating time, thus reducing the frequency of injection. According to these techniques, physiologically active proteins and peptides are not provided in a sustained release form but rather in a long-acting form.

One of the most popular strategies used to reduce injection frequency is to attach a highly soluble polymer such as polyethylene glycol (hereinafter referred to as "PEG") to the surface of pharmaceutically active proteins or peptides. PEG can be non-specifically attached to the amine group of amino acids of proteins or peptides. PEGylation can provide water solubility to hydrophobic drugs and proteins and increases the hydrodynamic size of the agent to prolong the time in circulation when it is injected to the body (Sada et al., *J. Ferment Bioeng* 71, 137-139, 1991).

Recently, PEGylated interferon alpha has been commercialized in order to reduce the injection intervals. In addition, Kinstler et al. demonstrated that one injection of PEGylated granulocyte colony-stimulating factor (G-CSF) per week (one chemotherapy cycle) had the same medical effect as did triweekly injections of G-CSF (Kinstler et al., *Pharm Res* 12, 1883-1888, 1995). PEG-GCSF was commercially available under the tradename of "Neulast."

Since the PEGylation of a protein results from the non-specific covalent conjugation of PEG to the surface of the protein, the interaction of the protein with its receptor may be hindered at the PEGylated region, thus significantly decreasing the in vivo activity of the protein. In addition, PEGylation is somewhat cumbersome because the proteins pegylated at the physiologically active site must be removed during a purification process to leave behind the PEG-protein conjugates which have their activity decreased to the minimal degree possible. In this process, thus, the production yield of desired PEG-protein conjugates is significantly lowered, resulting in the economically unfavorable situation. In addition, as for some proteins that are unstable in aqueous solutions, attempts to conjugate with PEG has been failed.

Also, a glycoengineering technique has been used to reduce injection frequency and has now been commercialized. Elliot et al. reported the additional glycosylation of erythropoietin (EPO) by substituting amino acids at certain positions (*Nat Biotechnol* 21, 414-421, 2003; U.S. Pat. No. 7,217,689). The erythropoietin modified by glycoengineering technique is now commercially available under the tradename of "Aranesp" and it is known that the circulation in the blood stream, metabolism and excretion of the modified erythropoietin are retarded due to the addition of sugar chains with sialic acid at the terminus and the increased molecular weight. However, the glycoenginneeing technology to introduce additional glycosilation sites of the proteins has not been widely used, because the attachment or addition of sugar chains may cause inactivation of the physiologically active protein, and its ability to maintain in vivo stability of many proteins has not been proven. And the choice of sites of the physiologically active protein to which sugar chains can be additionally attached is very narrow. In addition, the glycoengineering technology is not easy to apply to low-molecular weight peptides.

The development of genetic engineering technology has allowed to enlarge the size of a physiologically active protein by fusion with a high-molecular weight protein (*Curr Opin Drug Discov Devel* 12, 284-295, 2009). For example, a physiologically active protein gene is fused to a human albumin gene and then expressed in yeast cells to produce a fusion protein (International Patent Publication Nos. WO 93/15199 and WO 93/15200). Examples of the physiologically active protein fused to albumin include granulocyte colony stimulating factor (Halpern et al., *Pharm Res* 19, 1720-1729, 2002), human growth hormone (Osborn et al., *Eur J Pharmacol* 456, 149-158, 2002), glucagon like peptide-1 (Baggio et al., Diabetes 53, 2492-2500, 2004), and interferon alpha (Osborn et al., *J Pharmacol Exp Ther* 303, 540-548, 2002).

In the case of recombinant fusion technology, fusion proteins with transferrin are also known. For example, U.S. Pat. No. 7,176,278 discloses a fusion molecule in which glucagon like peptide-1 is fused to native transferrin or aglycosylated transferrin and becomes increased in vivo half-life.

Meanwhile, the in vivo half-life of a protein can be extended by fusion to an immunoglobulin (Ig) Fc fragment (U.S. Pat. Nos. 5,116,964 and 5,605,690). A fusion gene of TNF-α receptor fragment and IgG1 Fc fragment was expressed in an animal cell (Chinese hamster ovary, CHO) transformed with the gene encoding the fusion protein and the fusion protein is now commercially available (tradename: Enbrel) after approval of USFDA as a therapeutic agent for rheumatoid arthritis. Further, Wang (Qinghua Wang; WO 2007/012188) extended the in vivo half-life of GLP-1 ($t_{1/2}$<2 min) or exendin-4 with short half-life by fusion to an Ig Fc fragment.

Even if Ig Fc is widely used as a carrier for fusion proteins in order to increase in vivo half-life, IgG1 Fc retains its own antibody-dependent cell cytotoxicity (ADCC) or complement dependent cytotoxicity (CDC). Hence, when injected into the body, a fusion protein of a physiologically active protein with IgG1 Fc may cause complex immune responses. In addition, repeated administration of Fc fusion proteins for a long period of time may produce undesired antibodies. Accordingly, the use of IgG1 Fc fusion proteins has limitation in clinical application.

Korean Patent No. 10-0725315 discloses a protein complex using an immunoglobulin fragment and a method for the preparation thereof in which a physiologically active protein is fused to IgG Fc via PEG. The "protein complex" having a structure of physiologically active protein-PEG-Fc has a longer in vivo half-life than the physiologically active protein as measured by pharmacokinetic assay. However, the similar drawbacks or problems shown in Fc fusion method can be also observed in "protein complex" because a physiologically active protein and an Fc fragment are chemically bonded by PEG molecule.

Another example of the use of immunoglobulin in enhancing the in vivo stability of a peptide drug is the fusion of an entire IgG antibody molecule and a low-molecular peptide (Rader et al, *Proc. Natl. Acad. Sci. U.S.A.* 100, 5396-5400, 2003, Doppalapudi et al., *Bioorg & Med Chem* 17, 501-506, 2007). However, this technique, called "CovX-Body," cannot be applied to large-molecular weight proteins and its use is limited due to the problems generated upon the production of the Fc fusion proteins or the PEG fusion proteins.

As described above, many attempts have been made to fuse a biopolymer to a physiologically active protein or therapeutic peptide, but can be applied only to a limited range of proteins or peptides for the following reasons: in vivo residency time is not sufficiently long enough to develop the fusion protein for medicinal use; remarkably low production yield resulting in economically unfavorable situation; undesired immune responses when used for a long time; and the undesirable residual presence of toxic chemical derivatives when used for the conjugation with proteins or peptides. There is, therefore, a need for novel fusion proteins or peptides that can extend the in vivo half-life of physiologically active proteins or peptides, with the minimal loss of in vivo activity.

DISCLOSURE

Technical Problem

Leading to the present invention, intensive and thorough research into fusion proteins or peptides that have an extended in vivo half-life and minimalized loss of in vivo activity, conducted by the present inventors, resulted in the finding that alpha-1 antitrypsin or a variant thereof allows a physiologically active protein or peptide fused thereto to maintain sustained circulation in vivo and thus to have increased in vivo stability and in vivo half-life ($T_{1/2}$) compared to the protein or peptide on its own.

Technical Solution

The present invention provides an in vivo half-life-extended fusion protein or peptide with the sustained circulation thereof maintained, and a method for extending the in vivo half-life of a protein or peptide using the same.

BEST MODE

Figure 1:
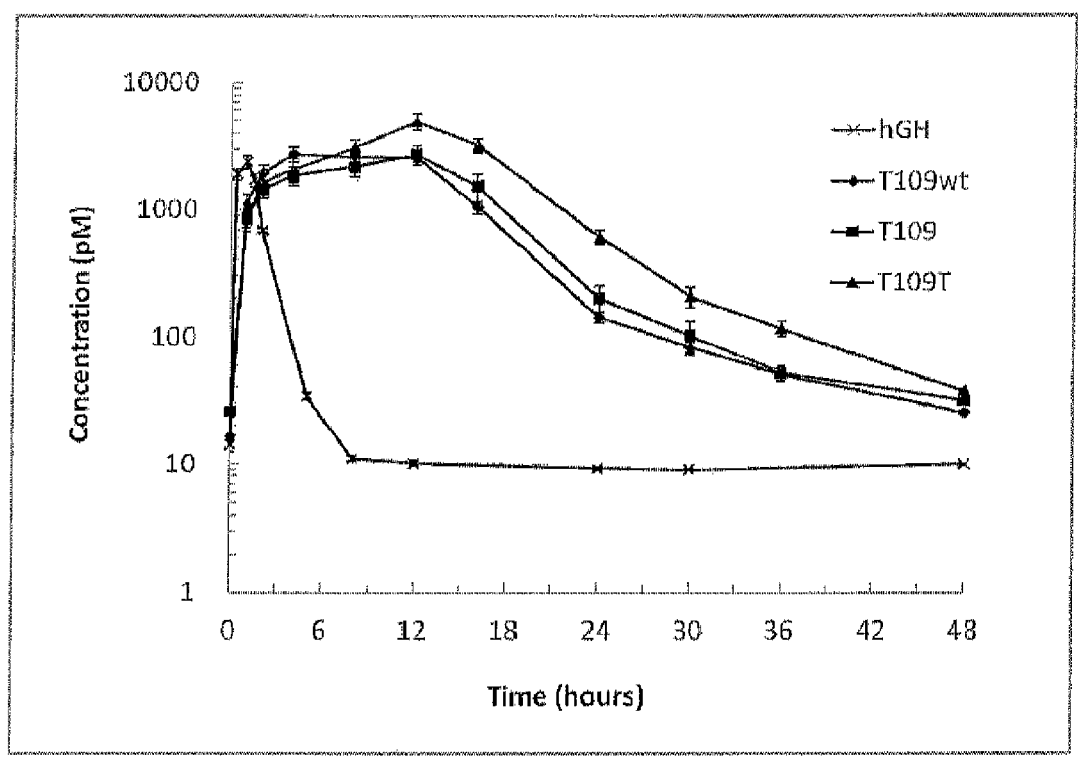
FIG. 1 is a graph demonstrating pharmacokinetic behaviors of the human growth hormone/alpha-1 antitrypsin fusion [T109wt: α1AT/hGH], the human growth hormone/alpha-1 antitrypsin monovariant fusion [T109: α1AT(P357N)/hGH], and the human growth hormone/alpha-1 antitrypsin divariant fusion [T109T: α1AT(P357N, S359T)/hGH].

In accordance with an aspect thereof, the present invention provides an in vivo half-life-extended fusion protein or peptide in which a physiologically active protein or peptide is fused to alpha-1 antitrypsin, whereby the physiologically active protein or peptide can be circulated in a sustained manner in vivo.

In accordance with another aspect thereof, the present invention provides an in vivo half-life-extended fusion protein or peptide in which a physiologically active protein or peptide is fused to an alpha-1 antitrypsin variant mutated at one or more amino acid residues, wherey the physiologically active protein or peptide can be circulated in a sustained manner in vivo.

In accordance with a further aspect thereof, the present invention provides a method for extending the in vivo half-life of a physiologically active protein or peptide, comprising fusing the physiologically active protein or peptide to alpha-1 antitrypsin or an alpha-1 antitrypsin variant having one or more mutated amino acids, whereby the physiologically active protein or peptide can be circulated in a sustained manner in vivo.

Below, a detailed description is given of the present invention.

The fusion protein or peptide according to the present invention features the use of alpha-1 antitrypsin or an alpha-1 antitrypsin variant to maintain the sustained circulation of a physiologically active protein or peptide to extend the in vivo half-life by fusing the physiologically active protein or peptide thereto.

As used herein, the term "fusion protein/fusion polypeptide" means a novel protein molecule in which a physiologically active protein with a large molecular weight is fused to the N- or C-terminus of alpha-1 antitrypsin or an alpha-1 antitrypsin variant. Likewise, the term "fusion peptide," as used herein, means a novel peptide molecule in which a physiologically active peptide with a low molecular weight is fused to the N- or C-terminus of alpha-1 antitrypsin or an alpha-1 antitrypsin variant.

The physiologically active protein or peptide may be fused directly or via a linker consisting of amino acids to alpha-1 antitrypsin or an alpha-1 antitrypsin variant mutated with one or more amino acids.

Preferably, a gene recombination technique is used to fuse the physiologically active protein or peptide to alpha-1 antitrypsin or an alpha-1 antitrypsin variant mutated at one or more amino acids. Alternatively, a linker well known in the art may be used for the fusion of the physiologically active protein or peptide to the N- or C-terminus or a free group of alpha-1 antitrypsin or an alpha-1 antitrypsin variant mutated at one or more amino acids.

Among the physiologically active proteins are hormones and their receptors, biological response modifiers and their receptors, cytokines and their receptors, enzymes, antibodies, and antibody fragments. Concrete examples of the physiologically active protein include human growth hormone (hGH), insulin, follicle-stimulating hormone (FSH), human chorionic gonadotropin, parathyroid hormone (PTH), erythropoietin (EPO), thrombopoietin (TPO), granulocyte colony stimulating factor (G-CSF), granulocyte macrophage colony-stimulating factor (GM-CSF), interferon alpha, interferon beta, interferon gamma, interleukins, macrophage activating factor, tumor necrosis factor, tissue plasminogen activator, coagulation factor VII, VIIa, VIII and IX, human bone morphogenic protein 2 (hBMP2), keratinocyte growth factor (KGF), platelet-derived growth factor (PDGF), glucocerebrosidase, α-galactosidase A, α-L-iduronidase, iduronate-2-sulfatase, lactase, adenosine deaminase, butyrylcholinesterase, chitinase, glutamate decarboxylase, imiglucerase, lipase, uricase, platelet-activating factor acetylhydrolase, neutral endopeptidase, urokinase, streptokinase, myeloperoxidase, superoxide dismutase, botulinum toxin, collagenase, hyaluronidase, L-asparaginase, monoclonal antibodies, polyclonal antibodies, scFv, Fab, Fab', F(ab')$_2$ and Fd, but are not limited thereto.

Examples of the physiologically active peptide include glucagon-like peptide-1 (GLP-1) and its analogs, exendin and its analogs, somatostatin and its analogs, luteinizing hormone-releasing hormone (LHRH) agonist and antagonist, adrenocorticotropic hormone, growth hormone-releasing hormone, oxytocin, thymosin alpha-1, corticotropin-releasing factor, calcitonin, bivalirudin, vasopressin analogues and fragments of physiologically active proteins, but are not limited thereto.

Alpha-1 antitrypsin is a mammalian serum protein of about 50,000 Daltons and present in high quantity in the blood about 2 mg/mL (Robin W. C. et al., *Nature* 298, 329-334, 1982). Alpha-1 antitrypsin is also referred to as alpha-1 protease inhibitor because it inhibits a wide variety of proteases. In conjunction with known diseases, however, it has the predominant function of protecting lung tissues from neutrophil elastase (Beatty et al., *J Biol Chem* 255, 3931-3934, 1980). In the absence of alpha-1 antitrypsin, neutrophil elastase is free to break down elastin, which contributes to the elasticity of the lungs, resulting in respiratory complications such as emphysema. Disorders of this protein include alpha 1-antitrypsin deficiency, a hereditary disorder. Alpha-1 antitrypsin extracted from serum has been commercially available as a therapeutic agent for emphysema under the tradename of "Prolastin" since it was approved by the FDA. The stability and safety of Prolastin have been proven and it is intravenously injected at a dose of 60 mg/kg per week. In addition, alpha-1 antitrypsin itself is known to have an in vivo half-life of about 5-6 days (Weweres, M D, et al., *N. Engl J Med* 316, 1055-1062, 1987). This provides a theoretical basis on which alpha-1 antitrypsin which is safe to the body even if it is administered in a large amount can function to increase the in vivo half-life of a physiologically active protein or peptide by fusion there between. The role as a protease inhibitor and the structure of alpha-1 antitrypsin are well known (Elliott, P. et al., *JMB* 275, 419-425, 1998). The P1 amino acid residue (position 358 from the N-terminal) in alpha-1 antitrypsin is methionine, a residue essential for binding elastase. The protein is also known to inhibit a wide variety of proteases including trypsin, chymostrypsin, thrombin, and elastase. The alpha-1 antitrypsin gene is highly pleiomorphic with over 100 alleles identified to date, the phenotypes of which are determined using IEF (isoelectric focusing) and assigned a letter code (A to Z) (Stoller et al., *The Lancet*, 365, 2225-2236, 2005). The family of M alleles, most prevalent among the alleles, is referred to as M, and is further divided into subtypes, such as M1 (Val$^{213}$), M1 (Ala$^{213}$), M2 and M3, according to the amino acid sequence mutations. Hence, the alpha-1 antitrypsin used in the present invention is a specific subtype belonging to the family of M alleles, and other subtypes are also used with the same effect.

The alpha-1 antitrypsin variant may be prepared by site-directed mutagenesis at one or more amino acids. For example, the alpha-1 antitrypsin variant may have asparagine at position 357 of P2 in substitution for proline. In addition to the replacement of P2 asparagine for proline at position 357, the alpha-1 antitrypsin variant may have one or more other mutant amino acids at other positions. In detail, the alpha-1 antitrypsin variant may have asparagine instead of proline at position 357 and optionally threonine instead of serine at position 359 and/or serine instead of cysteine at position 232. The alpha-1 antitrypsin variant useful in the present invention may be selected from among the alpha-1 antitrypsin monovariant [α1AT(P357N)], the alpha-1 antitrypsin divariant [α1AT(P357N, S359T)], the alpha-1 antitrypsin divariant 2[α1AT(P357N, C232S)], and the alpha-1 antitrypsin trivariant [α1AT(P357N, C232S, S359T)].

The alpha-1 antitrypsin monovariant [α1AT(P357N)] results from the replacement of proline (Pro) with asparagine (Asn) at position 357 of P2 from the N-terminus. This alpha-1 antitrypsin variant is characterized by the generation of a new N-glycosylation site Asn-X-Ser, which contributes to the function of neutralizing the inhibitory activity of alpha-1 antitrypsin as a protease inhibitor and also minimizing the immunogenicity attributable to the amino acid substitution upon injection.

The alpha-1 antitrypsin divariant [α1AT(P357N, S359T)] results from the replacement of proline with asparagine at position 357 of P2 and serine with threonine at position 359. This alpha-1 antitrypsin variant is characterized by the generation of a new N-glycosylation site Asn-X-Thr, which contributes to the function of neutralizing the inhibitory activity of alpha-1 antitrypsin as a protease inhibitor and minimizing the immunogenicity attributable to the amino acid substitution upon injection.

The alpha-1 antitrypsin divariant 2 [α1AT(P357N, C232S)] results from the replacement of proline with asparagine at position 357 of P2 and cysteine with serine at position 232. This alpha-1 antitrypsin divariant 2 is characterized by the generation of a new N-glycosylation site Asn-X-Ser, which contributes to the function of neutralizing the activity of alpha-1 antitrypsin as a protease inhibitor and minimizing the immunogenicity attributable to the amino acid substitution upon injection, and additionally prevention of a dimer formation mediated by the free cysteine.

Resulting from the replacement of proline with asparagine at position 357 of P2, cysteine with serine at position 232, and serine with threonine at position 359, the alpha-1 antitrypsin trivariant [α1AT(P357N, C232S, S359T)] is characterized by the generation of a new N-glycosylation site Asn-X-Thr, which contributes to the function of neutralizing the inhibitory activity of alpha-1 antitrypsin as a protease inhibitor and minimizing the immunogenicity attributable to the amino acid substitution upon injection, and additionally preventing of a dimer formation mediated by the free cysteine.

Among the fusion proteins or peptides of the present invention are human growth hormone/alpha-1 antitrypsin [T109wt: α1AT/hGH] (SEQ ID NO: 1), human growth hormone/alpha-1 antitrypsin monovariant [T109: α1AT(P357N)/hGH] (SEQ ID NO: 2), human growth hormone/alpha-1 antitrypsin divariant [T109T: α1AT(P357N, S359T)/hGH] (SEQ ID NO: 3), human interferon alpha/alpha-1 antitrypsin monovariant [T502: α1AT(P357N)/IFN-α] (SEQ ID NO: 4), granulocyte colony-stimulating factor/alpha-1 antitrypsin divariant [T602S: α1AT(P357N, C232S)/G-CSF] (SEQ ID NO: 5), granulocyte colony-stimulating factor/alpha-1 antitrypsin trivariant [T602ST: α1AT(P357N, C232S, S359T)/G-CSF] (SEQ ID NO: 6), and exendin-4/alpha-1 antitrypsin monovariant [T304: Exendin-4/α1AT(P357N)] (SEQ ID NO: 7).

All of the fusion proteins or peptides described herein human growth hormone/alpha-1 antitrypsin [T109wt: α1AT/hGH], human growth hormone/alpha-1 antitrypsin monovariant [T109: α1AT(P357N)/hGH], human growth hormone/alpha-1 antitrypsin divariant [T109T: α1AT(P357N, S359T)/hGH], human interferon alpha/alpha-1 antitrypsin monovariant [T502: α1AT(P357N)/IFN-α], granulocyte colony-stimulating factor/alpha-1 antitrypsin divariant [T602S: α1AT(P357N, C232S)/G-CSF], granulocyte colony-stimulating factor/alpha-1 antitrypsin trivariant

[T602ST: α1AT(P357N, C232S, S359T)/G-CSF], and exendin-4/alpha-1 antitrypsin monovariant [T304: Exendin-4/α1AT(P357N)] are significantly increased in serum half-life ($t_{1/2}$) and show excellent in vivo stability, as compared to the physiologically active proteins or peptides themselves.

When injected into pituitary gland-removed rats, the human growth hormone/alpha-1 antitrypsin monovariant fusion [T109: α1AT(P357N)/hGH] was found to induce the animals to gain weight. The level of leucocytes in rats was increased when they were injected with the granulocyte colony-stimulating factor/alpha-1 antitrypsin divariant fusion [T602S: α1AT(P357N, C232S)/G-CSF] or the granulocyte colony-stimulating factor/alpha-1 antitrypsin trivariant fusion [T602ST: α1AT(P357N, C232S, S359T)/G-CSF]. The group administered with the exendin-4/alpha-1 antitrypsin monovariant fusion [T304: Exendin-4/α1AT(P357N)] showed lower blood sugar levels than did the groups administered with exendin-4 and this low blood sugar level was maintained for at least 24 hours after administration. Thus, the fusion proteins or peptides according to the present invention retain in vivo activity for a long period of time.

In addition, the fusion proteins or peptides, human growth hormone/alpha-1 antitrypsin [T109wt: α1AT/hGH], human growth hormone/alpha-1 antitrypsin monovariant [T109: α1AT(P357N)/hGH], human growth hormone/alpha-1 antitrypsin divariant [T109T: α1AT(P357N, S359T)/hGH], granulocyte colony-stimulating factor/alpha-1 antitrypsin divariant [T602S: α1AT(P357N, C232S)/G-CSF] and granulocyte colony-stimulating factor/alpha-1 antitrypsin trivariant [T602ST: α1AT(P357N, C232S, S359T)/G-CSF] have similar intracellular activity ($EC_{50}$) and therefore, their activities do not significantly vary depending on the type of the carriers, that is, alpha-1 antitrypsin and alpha-1 antitrypsin variants.

Further, the human growth hormone/alpha-1 antitrypsin fusion [T109wt: α1AT/hGH] of the present invention shows excellent inhibitory activity against trypsin and human neutrophil elastase while the human growth hormone/alpha-1 antitrypsin monovariant fusion [T109: α1AT(P357N)/hGH] has very low inhibitory activity against trypsin and human neutrophil elastase. Accordingly, the fact that the human growth hormone/alpha-1 antitrypsin fusion [T109wt: α1AT/hGH] and the human growth hormone/alpha-1 antitrypsin monovariant fusion [T109: α1AT(P357N)/hGH] increase in vivo half-life by sustained circulation is not dependent on the inherent property of alpha-1 antitrypsin.

As described above, the fusion proteins or peptides according to the present invention are increased in serum half-life ($T_{1/2}$) through sustained circulation, and thus have higher in vivo stability, compared to the physiologically active proteins or peptides themselves. Consequently, the fusion proteins or peptides of the present invention can be applied to the development of the sustained circulation dosage forms of the protein or peptide drugs.

MODE FOR INVENTION

A better understanding of the present invention may be obtained through the following examples which are set forth to illustrate, but are not to be construed as limiting the present invention.

Example 1

Preparation of Human Growth Hormone/Alpha-1 Antitrypsin Fusion [T109wt: α1AT/hGH]

1. Construction of Expression Vector, pSNAT

For use in the expression of human growth hormone fused to the C-terminus of alpha-1 antitrypsin, the expression vector pSNAT which carried alpha-1 antitrypsin was constructed. In detail, alpha-1 antitrypsin gene was obtained from the vector hMU001448 (KRIBB) by PCR using a pair of primers ALT21 (SEQ ID NO: 8) and ALT30 (SEQ ID NO: 9), which were designed to fuse human growth hormone to the C-terminus of alpha-1 antitrypsin. The primer ALT30 was also designed to have a linker which would give flexibility necessary for the maintenance of the fusion proteins. The amplified nucleotide was digested with two restriction enzymes XhoI and BamHI and cloned into pSGHV0 (GenBank Accession No. AF285183) resulting in a recombinant vector, called pSNAT.

2. Construction of Human Growth Hormone/Alpha-1 Antitrypsin Vector [T109wt, α1AT/hGH]

A human growth hormone (hGH) gene was amplified from the IOH45734 vector (Invitrogen) by PCR using a pair of primers DH22 (SEQ ID NO: 10) and ALT12 (SEQ ID NO: 11). The PCR product thus obtained was digested with two restriction enzymes BamHI and NotI, and cloned to pSNAT at the same restriction site BamHI/NotI to make a recombinant expression vector, called T109wt (SEQ ID NO: 1).

3. Expression of Human Growth Hormone/Alpha-1 Antitrypsin Fusion (T109wt)

The human growth hormone/alpha-1 antitrypsin fusion (T109wt) prepared above in 1-2 was expressed in Chinese hamster ovary cells (CHO-K1). CHO-K1 was maintained in DMEM (Dulbecco's Modified Eagle Media) supplemented with 10% FBS (Fetal Bovine Serum) and antibiotics at 37° C. under a 5% $CO_2$ condition. One day before the introduction of the human growth hormone/alpha-1 antitrypsin fusion (T109wt) thereinto, the cells were inoculated at a density of $1 \times 10^6$ cells into a 100 mm culture dish. To 800 μL of DMEM free of FBS and antibiotics was added 5 μg of the human growth hormone/alpha-1 antitrypsin fusion (T109wt) and the mixture was incubated at room temperature for 1 min, mixed with 20 μg of PEI (Polyethylenimine, linear, Polysciences Inc (Cat. no: 23966, MW-25,000)) and left at room temperature for 10-15 min. Meanwhile, the cells incubated for one day were washed with PBS and provided with 6 mL of fresh DMEM. The human growth hormone/alpha-1 antitrypsin fusion (T109wt) left for 10-15 min at room temperature was added to the culture dish. Next day, the cells were washed with PBS and provided with FBS-free IMDM (Cat. No 12200-028, Gibco, Iscove's Modified Dulbecco's Medium) to identify the expression of the protein.

4. Purification of Human Growth Hormone/Alpha-1 Antitrypsin Fusion (T109wt)

After being expressed in Chinese hamster ovary cells (CHO0K1) as described in 1-3 above, the T109wt protein was purified as follows. In detail, because the human growth hormone/alpha-1 antitrypsin fusion (T109wt) was secreted to the medium, the cell culture was centrifuged so that the supernatant could be collected. This supernatant was diluted in an equilibrium buffer solution (20 mM sodium phosphate, pH 8.0), loaded to a Q-Sepharose column (GE Healthcare, U.S.A.) previously equilibrated with the equilibrium buffer solution, and sufficiently washed with the equilibrium buffer solution, followed by elution with an increasing NaCl concentration gradient of an eluent (0-400 mM NaCl, 20 mM sodium phosphate, pH 8.0). The protein eluate was mixed with a salt, loaded to an equilibrated Phenyl-Sepharose column (GE Healthcare, U.S.A), and washed with a sufficient amount of the equilibrium buffer solution, followed by elution with a decreasing NaCl concentration gradient of an eluent (2-0 M NaCl, 20 mM sodium phosphate, pH 6.8). The protein fraction was concentrated with the aid of Vivaspin20 (GE Healthcare, U.S.A.) to produce highly purified T109wt.

Example 2

Preparation of Human Growth Hormone/Alpha-1 Antitrypsin Monovariant Fusion [T109: α1AT(P357N)/hGH]

1. Preparation of Alpha-1 Antitrypsin Monovariant (pDHT3N Cloning Vector)

Because alpha-1 antitrypsin used for a fusion carrier in the fusion molecule has an inhibitory activity itself, the inhibitor activity of alpha-1 antitrypsin was substantially decreased by making a variant of alpha-1 antitrypsin. In this regard, an alpha-1 antitrypsin gene was amplified from the vector hMU001448 (KRIBB) by PCR, and cloned into the yT&A vector to produce a recombinant vector pDHT3. Afterwards, substitution mutation of the proline residue at position 357 of P2 with asparagine for N-glycosylation was performed using a pair of primers ALT1 (SEQ ID NO: 12) and ALT2 (SEQ ID NO: 13) with the aid of a mutagenesis kit (Stratagene, QuikChange II Cat No. 200523-5) to produce a cloning vector pDHT3N.

2. Construction of Expression Vector pSNATN

For use in the expression of human growth hormone fused to the C-terminus of the inactivated alpha-1 antitrypsin, the expression vector pSNATN which carried the alpha-1 antitrypsin monovariant was constructed. In detail, an alpha-1 antitrypsin monovariant gene was obtained from the vector pDHT3N by PCR using a pair of primers ALT14 (SEQ ID NO: 14) and ALT30 (SEQ ID NO: 9) and cloned into pSNAT digested with two restriction enzymes EcoRV and BamHI to afford a recombinant vector, called pSNATN.

3. Construction of Human Growth Hormone/Alpha-1 Antitrypsin Monovariant Vector [T109, α1AT(P357N)/hGH]

The human growth hormone gene amplified in Example 1-2 was inserted into pSNATN at the restriction site BamHI/NotI to afford a recombinant expression vector, called T109 (SEQ ID NO: 2).

4. Expression of Human Growth Hormone/Alpha-1 Antitrypsin Monovariant Fusion (T109)

The expression of the human growth hormone/alpha-1 antitrypsin monovariant fusion (T109) in Chinese hamster ovary cells (CHO-K1) was identified in the same procedure as in Example 1-3.

5. Purification of Human Growth Hormone/Alpha-1 Antitrypsin Monovariant Fusion (T109)

The human growth hormone/alpha-1 antitrypsin monovariant fusion (T109) was purified in the same manner as in Example 1-4.

Example 3

Preparation of Human Growth Hormone/Alpha-Antitrypsin Divariant Fusion [T109T: α1AT(P357N, S359T)/hGH]

1. Preparation of Alpha-1 Antitrypsin Divariant (pDHT3NT Cloning Vector)

For use in the preparation of inactivated alpha-1 antitrypsin by introduction of glycosylation site at the active site of the molecule, alpha-1 antitrypsin was double mutated to decrease its activity and achieve the homogeneity of glycosylation. In this regard, substitution of the serine residue at position 359 with threonine for homogeneity of glycosylation formation was performed on the N-glycosylation-induced pDHT3N cloning vector which carries the alpha-1 antitrypsin monovariant which was decreased in activity by mutating proline at position 357 of P2 into asparagine, using a pair of primers ALT82 (SEQ ID NO: 15) and ALT83 (SEQ ID NO: 16) with the aid of a mutagenesis kit (Enzynomics, EZchange Cat No. EM020) to produce a cloning vector, called pDHT3NT.

2. Construction of Expression Vector pSNATNT

For use in the expression of human growth hormone fused to the C-terminus of the alpha-1 antitrypsin divariant, which has the homogeneity of glycosylation and had decreased activity, an expression vector pSNATNT was constructed. In this regard, an alpha-1 antitrypsin divariant gene was amplified from pDHT3NT by PCR using a pair of primers ALT14 (SEQ ID NO: 14) and ALT30 (SEQ ID NO: 9), designed to fuse human growth hormone to the C-terminus of the alpha-1 antitrypsin divariant, and cloned to pSNAT previously treated with two restriction enzymes EcoRV and BamHI, to give a recombinant expression vector, called pSNATNT.

3. Construction of Human Growth Hormone/Alpha-1 Antitrypsin Divariant Vector [T109T, α1AT(P357N, S359T)/hGH]

The human growth hormone nucleotide amplified in Example 1-2 was cloned to pSNATNT at the restriction site BamHI/NotI to give an expression vector, called T109T (SEQ ID NO: 3).

4. Expression of Human Growth Hormone/Alpha-1 Antitrypsin divariant fusion (T109T)

The expression of human growth hormone/alpha-1 antitrypsin divariant fusion (T109T) in Chinese hamster ovary cells (CHO-K1) was identified in the same manner as in Example 1-3.

5. Purification of Human Growth Hormone/Alpha-1 Antitrypsin Divariant Fusion (T109T)

The human growth hormone/alpha-1 antitrypsin divariant fusion (T109T) was purified in the same manner as in Example 1-4.

Example 4

Preparation of Human Interferon Alpha/Alpha-1 Antitrypsin Monovariant Fusion [T502: α1AT(P357N)/IFN-α]

1. Construction of Human Interferon Alpha/Alpha-1 Antitrypsin Monovariant Vector [T502, α1AT(P357N)/IFN-α]

A human interferon alpha (IFN-α) gene was amplified from the MHS1010-98051913 vector (Open biosystems) by PCR using a pair of primers ALT45 (SEQ ID NO: 17) and ALT49 (SEQ ID NO: 18). The PCR product thus obtained was double digested with BamHI and NotI and then cloned into pSNATN at the restriction site BamHI/NotI to give a recombinant expression vector, called T502 (SEQ ID NO: 4).

2. Expression of Human Interferon Alpha/Alpha-1 Antitrypsin Monovariant (T502)

The expression of human interferon alpha/alpha-1 antitrypsin monovariant fusion (T502) in Chinese hamster ovary cells (CHO-K1) was identified in the same manner as in Example 1-3.

3. Purification of Human Interferon Alpha/Alpha-1 Antitrypsin Monovariant (T502)

The human interferon alpha/alpha-1 antitrypsin monovariant fusion (T502) was purified in the same manner as in Example 1-4.

Example 5

Preparation of Granulocyte Colony-Stimulating Factor/Alpha-1 Antitrypsin Divariant Fusion [T602S: α1AT(P357N, C232S)/G-CSF]

1. Preparation of Alpha-1 Antitrypsin Divariant 2 (pDHT3NS Cloning Vector)

For use in the preparation of protein or peptide therapeutic agents, alpha-1 antitrypsin divariant 2 was prepared by mutating alpha-1 antitrypsin to decrease the inherent activity of alpha-1 antitrypsin and eliminate the possibility of protein denaturation resulting from cystein-mediated dimer formation. In this context, substitution mutation of the cystein residue at position 232 with threonine was performed on the N-glycosylation-induced pDHT3N cloning vector which carries the alpha-1 antitrypsin monovariant decreased in activity by mutating proline at position 357 of P2 into asparagine, using a pair of primers ALT52 (SEQ ID NO: 19) and ALT53 (SEQ ID NO: 20) with the aid of a mutagenesis kit (Stratagene, QuikChange II Cat No. 200523-5) to produce a cloning vector, called pDHT3NS.

2. Construction of Expression Vector pSNATNS

For use in the expression of granulocyte colony-stimulating factor fused to the C-terminus of the alpha-1 antitrypsin divariant 2, which has decreased inhibitor activity, an expression vector pSNATNS was constructed. In this regard, an alpha-1 antitrypsin divariant 2 gene was amplified from pDHT3NS by PCR using a pair of primers ALT14 (SEQ ID NO: 14) and ALT30 (SEQ ID NO: 9), designed to fuse granulocyte colony-stimulating factor to the C-terminus of the alpha-1 antitrypsin divariant 2, and was cloned to pSNAT previously treated with two restriction enzymes BstEII and BamHI, to give a recombinant expression vector, called pSNATNS.

3. Construction of Granulocyte Colony-Stimulating Factor/Alpha-1 Antitrypsin Divariant 2 Vector [T602S, α1AT (P357N, C232S)/G-CSF]

A granulocyte colony-stimulating factor (G-CSF) gene was amplified from IHS1380-97652343 (Open biosystems) by PCR using a pair of primers ALT56 (SEQ ID NO: 21) and ALT57 (SEQ ID NO: 22). The PCR product thus obtained was double digested with BamHI and NotI and cloned to pSNATNS at the restriction site BamHI/NotI to give a recombinant expression vector, called T602S (SEQ ID NO: 5).

4. Expression of Granulocyte Colony-Stimulating Factor/Alpha-1 Antitrypsin divariant fusion (T602S)

The expression of granulocyte colony-stimulating factor/alpha-1 antitrypsin divariant fusion (T602S) in Chinese hamster ovary cells (CHO-K1) was identified in the same manner as in Example 1-3.

5. Purification of Granulocyte Colony-Stimulating Factor/Alpha-1 Antitrypsin divariant fusion (T602S)

The granulocyte colony-stimulating factor/alpha-1 antitrypsin divariant fusion (T602S) was purified in the same manner as in Example 1-4.

Example 6

Preparation of Granulocyte Colony-Stimulating Factor/Alpha-1 Antitrypsin Trivariant Fusion [T602ST: α1AT(P357N, C232S, S359T)/G-CSF]

1. Preparation of Alpha-1 Antitrypsin Trivariant (pDHT3NST Cloning Vector)

For use in the preparation of protein or peptide therapeutic agents, an alpha-1 antitrypsin trivariant was prepared by mutating the alpha-1 antitrypsin divariant to achieve the homogeneity of glycosylation. In this regard, using a mutagenesis kit (Enzynomics, EZchange Cat No. EM020) in the presence of a pair of primers ALT82 (SEQ ID NO: 15) and ALT83 (SEQ ID NO: 16), substitution of serine residue at position 359 with threonine for homogeneity of glycosylation was performed on the N-glycosylation-induced pDHT3NS cloning vector carrying the alpha-1 antitrypsin divariant 2 in which the inherent activity was decreased as a result of substitution of the proline at position 357 of P2 into asparagine and the likelihood of protein denaturation attributable to cystein-mediated dimer formation was removed as a result of substitution of cystein at position 232 with serine.

2. Construction of Expression Vector pSNATNST

For use in the expression of granulocyte colony-stimulating factor fused to the C-terminus of the alpha-1 antitrypsin trivariant, which has decreased activity, an expression vector pSNATNST was constructed. In this regard, an alpha-1 antitrypsin trivariant gene was amplified from pDHT3NST by PCR using a pair of primers ALT14 (SEQ ID NO: 14) and ALT30 (SEQ ID NO: 9), designed to fuse granulocyte colony-stimulating factor to the C-terminus of the alpha-1 antitrypsin trivariant, and was cloned to pSNAT previously treated with two restriction enzymes BstEII and BamHI, to give a recombinant expression vector, called pSNATNST.

3. Construction of Granulocyte Colony-Stimulating Factor/Alpha-1 Antitrypsin Trivariant Vector [T602ST, α1AT (P357N, C232S, S359T)/G-CSF]

A granulocyte colony-stimulating factor (G-CSF) gene was amplified from the IHS1380-97652343 vector (Open biosystems) by PCR using a pair of primers ALT56 (SEQ ID NO: 21) and ALT57 (SEQ ID NO: 22). The amplified nucleotide was double digested with BamHI and NotI and cloned into pSNATNST at the restriction site BamHI/NotI to give a recombinant expression vector, called 1602ST (SEQ ID NO: 6).

4. Expression of Granulocyte Colony-Stimulating Factor/Alpha-1 Antitrypsin Trivariant Fusion (T602ST)

The expression of granulocyte colony-stimulating factor/alpha-1 antitrypsin trivariant fusion (1602ST) in Chinese hamster ovary cells (CHO-K1) was identified in the same manner as in Example 1-3.

5. Purification of Granulocyte Colony-Stimulating Factor/Alpha-1 Antitrypsin Trivariant Fusion (T602ST)

The granulocyte colony-stimulating factor/alpha-1 antitrypsin trivariant fusion (T602ST) was purified in the same manner as in Example 1-4.

Example 7

Preparation of Exendin-4/Alpha-1 Antitrypsin Monovariant Fusion [T304: Exendin-4/α1AT(P357N)]

1. Construction of Expression Vector pSCAT

For use in the expression of exendin-4 fused to the N-terminus of alpha-1 antitrypsin, a pSCAT vector was constructed. In detail, alpha-1 antitrypsin to the N-terminus of which exendin-4 would be fused was amplified from the hMU001448 vector (KRIBB) by PCR using a pair of primers ALT21 (SEQ ID NO: 8) and ALT5 (SEQ ID NO: 23). The amplified nucleotide was digested with two restriction enzymes XhoI and NotI and cloned into pSGHV0 (GenBank Accession No. AF285183) to give a recombinant vector, called pSCAT.

2. Construction of Expression Vector pSCATN

For use in the expression of exendin-4 fused to the N-terminus of the inactivated alpha-1 antitrypsin monovariant, pSCATN was constructed. In this context, a gene encoding the alpha-1 antitrypsin monovariant to the N-terminus of which exendin-4 would be fused was obtained from the vector pDHT3N and cloned into pSCAT using two restriction enzymes EcoRV and NotI to give a recombinant vector, called pSCATN.

3. Preparation of Exendin-4

An exendin-4 gene was amplified by PCR using DH15 (sense codon, SEQ ID NO: 24) and DH16 (antisense codon, SEQ ID NO: 25).

4. Construction of Exendin-4/Alpha-1 Antitrypsin Monovariant [1304, Exendin-4/α1AT(P357N)]

An exendin-4 gene was amplified from the gene prepared in Example 7-3 by PCR using a pair of primers ALT44 (SEQ ID NO: 26) and ALT41 (SEQ ID NO: 27). This amplified nucleotide was double digested with XhoI and BamHI and cloned into pSCATN at the restriction site XhoI/BamHI to produce an exendin-4/alpha-1 antitrypsin monovariant vector (T304, SEQ ID NO: 7).

5. Expression of Exendin-4/Alpha-1 Antitrypsin Monovariant Fusion (T304)

The expression of the exendin-4/alpha-1 antitrypsin variant fusion (T304) in Chinese hamster ovary cells (CHO-K1) was identified in the same manner as in Example 1-3.

6. Purification of Exendin-4/Alpha-1 Antitrypsin Monovariant Fusion (T304)

The exendin-4/alpha-1 antitrypsin monovariant fusion (T304) was purified in the same manner as in Example 1-4.

Test Example 1

Enzyme Immunoassay of the Fusion Proteins or Peptides

Enzyme immunoassay was conducted to analyze the fusion proteins or peptides of the present invention as follows.

1. Enzyme Immunoassay of Human Growth Hormone (hGH), Human Growth Hormone/Alpha-1 Antitrypsin Fusion [T109wt: α1AT/hGH], Human Growth Hormone/Alpha-1 Antitrypsin Monovariant Fusion [T109: α1AT(P357N)/hGH] and Human Growth Hormone/Alpha-1 Antitrypsin divariant fusion [T109T: α1AT(P357N, S359T)/hGH]

An anti-human growth hormone monoclonal antibody (Medix Biochemica, Finland) was diluted to a concentration of 1-5 μg/mL in phosphate buffered saline (PBS) and the dilution was aliquoted in an amount of 100 μL/well onto a 96-well plate (Nunc, Denmark) and incubated at room temperature for 15-18 hrs. After the antibody remaining suspended was removed, PBS containing 1% bovine serum albumin was plated in an amount of 250 μL/well and incubated at room temperature for 2 hours. The plates were washed three times with wash buffer (0.05% Tween 20, PBS) and the solution was aspirated. Samples were diluted in PBS containing 1% bovine serum albumin and added to the 96-well plates before incubation at room temperature for 2 hrs. The 96-well plates were washed five times with wash buffer and 100 μL of the human growth hormone monoclonal antibody-biotin conjugate prepared using sulfo-NHS-biotin (Pierce biotechnology, U.S.A.) was added to each well of the 96-well plates and then incubated at room temperature for 2 hrs. The plates were washed five times with wash buffer and incubated with streptabidin-HRP at room temperature for 30 min. Again, the plates were washed five times with wash buffer and reacted with 100 μL of a mixture of TMB (3,3',5,5'-tetramethylbenzidine) and hydrogen peroxide per well for 30 min in a dark place. To each well was added 100 μL of 1 M sulfuric acid to terminate the reaction, followed by measuring absorbance at 450 nm on a VersaMax microplate reader (Molecular Device, U.S.A.). Values for each sample were calculated by regression analysis after a standard curve was plotted for a reference material.

2. Enzyme Immunoassay of Human Interferon Alpha (IFN-α), Human Interferon Alpha/Alpha-1 Antitrypsin Monovariant Fusion [T502: α1AT(P357N)/IFN-α]

The enzyme immunoassay of human interferon alpha (IFN-α) and human interferon alpha/alpha-1 antitrypsin monovariant fusion was conducted with Human IFN-α Matched Antibody Pairs for ELISA (bender Medsystems, Austria). The IFN-α antibody (10 μg/ml) was allowed to adhere to 96-well plates and blocked as described in Test Example 1-1. A dilution of the sample was reacted with the antibody at room temperature for 2 hrs with shaking. An anti-IFN-α-HRP conjugate was plated in an amount of 50 μL/well and reacted with the antibody at room temperature for 2 hrs with shaking. Subsequent processes were conducted in the same manner as in Test Example 1-1.

3. Enzyme Immunoassay of Granulocyte Colony-Stimulating Factor (G-CSF), Granulocyte Colony-Stimulating Factor/Alpha-1 Antitrypsin Divariant Fusion [T602S: α1AT(P357N, C232S)/G-CSF], Granulocyte Colony-Stimulating Factor/Alpha-1 Antitrypsin Trivariant Fusion [T602ST: α1AT(P357N, C232S, S359T)/G-CSF]

The same procedure as in Test Example 1 was repeated with the exception that an anti-granulocyte colony-stimulating factor (G-CSF) monoclonal antibody (RND systems, U.S.A.), instead of the anti-human growth hormone antibody, was diluted to a concentration of 1-5 μg/mL and granulocyte colony-stimulating factor polyclonal antibodies-biotin conjugate (RND systems, U.S.A.), instead of the human growth hormone monoclonal antibody-biotin conjugate, was used.

4. Enzyme Immunoassay of Exendin-4, Exendin-4/Alpha-1 Antitrypsin Monovariant Fusion [T304: Exendin-4/α1AT(P357N)]

The same procedure as in Test Example 1-1 was repeated, with the exception that anti-exendin-4 polyclonal antibodies (Peptron, Korea), instead of the anti-human growth hormone, were diluted to a concentration of 5-10 μg/mL in PBS and an exendin-4 monoclonal antibody-biotin conjugate, instead of the human growth hormone monoclonal antibody-biotin conjugate, was used.

As for the exendin-4/alpha-1 antitrypsin monovariant fusion (T304) prepared in Example 7, it was mixed with a Freund adjuvant (Sigma, U.S.A.) before injection into rats to produce antisera. The antibodies were purified using Protein G-Sepharose (GE Healthcare, U.S.A.). The purified antibodies were diluted to a concentration of 10-20 μL/mL in PBS, and 96-well plates were coated with the antibodies, and reacted with the exendin-4/alpha-1 antitrypsin monovariant fusion (T304) polyclonal antibody-biotin conjugate prepared using a sulfo-NHS-biotin conjugate (Pierce biotechnology, U.S.A.) in a similar manner to that of Test Example 1-1. The reactions with the sample and the conjugate were conducted while being shaken.

Test Example 2

Pharmacokinetic Assay of the Fusion Proteins or Peptides

To examine the pharmacokinetics of the fusion proteins or peptides, the following experiments were conducted.

1. Pharmacokinetics of Human Growth Hormone (hGH), Human Growth Hormone/Alpha-1 Antitrypsin Fusion [T109wt: α1AT/hGH], Human Growth Hormone/Alpha-1 Antitrypsin Monovariant Fusion [T109: α1AT(P357N)/hGH], Human Growth Hormone/Alpha-1 Antitrypsin Divariant Fusion [T109T: α1AT(P357N, S359T)/hGH]

Sprague-Dawley rats were used as experimental animals and three of them were administered with human growth hormone while five rats were assigned to each of the fusion-administered groups. The human growth hormone/alpha-1 antitrypsin fusion [T109wt: α1AT/hGH], the human growth hormone/alpha-1 antitrypsin monovariant fusion [T109: α1AT(P357N)/hGH], and the human growth hormone/alpha-1 antitrypsin divariant fusion [T109T: α1AT(P357N, S359T)/hGH], all prepared in Examples 1-3, were subcutaneously injected at a dose of 720 μg/kg into respective groups of Sprague-Dawley rats. The samples were diluted in PBS before injection. Blood samples were taken at 0, 1, 2, 4, 8, 12, 16, 24, 30 and 48 hrs after the injection, and centrifuged to obtain sera. For a control, Scitropin (SciGen, Singapore), a kind of human growth hormone, was subcutaneously injected at a dose of 200 μg/kg. PBS was used as a diluent. Blood samples were taken at 0, 0.33, 1, 2, 5, 8, 12, 18, 24, 30 and 48 hrs after the injection, and centrifuged to obtain sera. Each sample was analyzed in the same manner as the enzyme immunoassay of Test Example 1.

The pharmacokinetics of the human growth hormone/alpha-1 antitrypsin fusion [T109wt: α1AT/hGH], the human growth hormone/alpha-1 antitrypsin monovariant fusion [T109: α1AT(P357N)/hGH], and human growth hormone/alpha-1 antitrypsin divariant fusion [T109T: α1AT(P357N, S359T)/hGH] are plotted in FIG. 1.

As seen in FIG. 1, the human growth hormone/alpha-1 antitrypsin fusion [T109wt: α1AT/hGH] had a serum half-life ($t_{1/2}$) of 5.3 hrs and a time to peak serum concentration ($T_{max}$) of 8 hrs, the human growth hormone/alpha-1 antitrypsin monovariant fusion [T109: α1AT(P357N)/hGH] had a serum half-life ($t_{1/2}$) of 5.4 hrs and a $T_{max}$ of 12 hrs, and the human growth hormone/alpha-1 antitrypsin divariant fusion [T109T: α1AT(P357N, S359T)/hGH] had a serum half-life ($t_{1/2}$) of 4.9 hrs and a $T_{max}$ of 12.8 hrs. On the other hand, human growth hormone (hGH) had a serum half-life ($t_{1/2}$) of 0.8 hrs and a $T_{max}$ of 1 hr. Hence, all the human growth hormone/alpha-1 antitrypsin fusion [T109wt: α1AT/hGH], human growth hormone/alpha-1 antitrypsin monovarian fusion [T109: α1AT(P357N)/hGH], and human growth hormone/alpha-1 antitrypsin divariant fusion [T109T: α1AT(P357N, S359T)/hGH] were observed to have significantly increased in vivo stability over that of human growth hormone.

2. Pharmacokinetics of Human Interferon Alpha (IFN-α), Human Interferon Alpha/Alpha-1 Antitrypsin Monovariant Fusion [T502: α1AT(P357N)/IFN-α]

Sprague-Dawley rats were used as experimental animals and five rats were assigned to each test group. The human interferon alpha/alpha-1 antitrypsin monovariant fusion [T502: α1AT(P357N)/IFN-α] prepared in Example 4 was subcutaneously injected at a dose of 200 μg/kg into Sprague-Dawley rats of one test group, 0, 0.33, 1, 2, 5, 8, 12, 18, 24, 30, 48, 72 and 96 hrs after which blood samples were taken, and centrifuged to obtain sera. As a control, human interferon alpha (IFN-α, Intermax alpha, LG Life Sciences, Korea) was subcutaneously injected at a dose of 60 μg/kg to rats, 0, 0.33, 1, 2, 5, 8, 12, 18, and 24 hrs after which blood samples were taken and centrifuged to obtain sera. Each sample was analyzed in the same manner as the enzyme immunoassay of Test Example 1.

Figure 2:
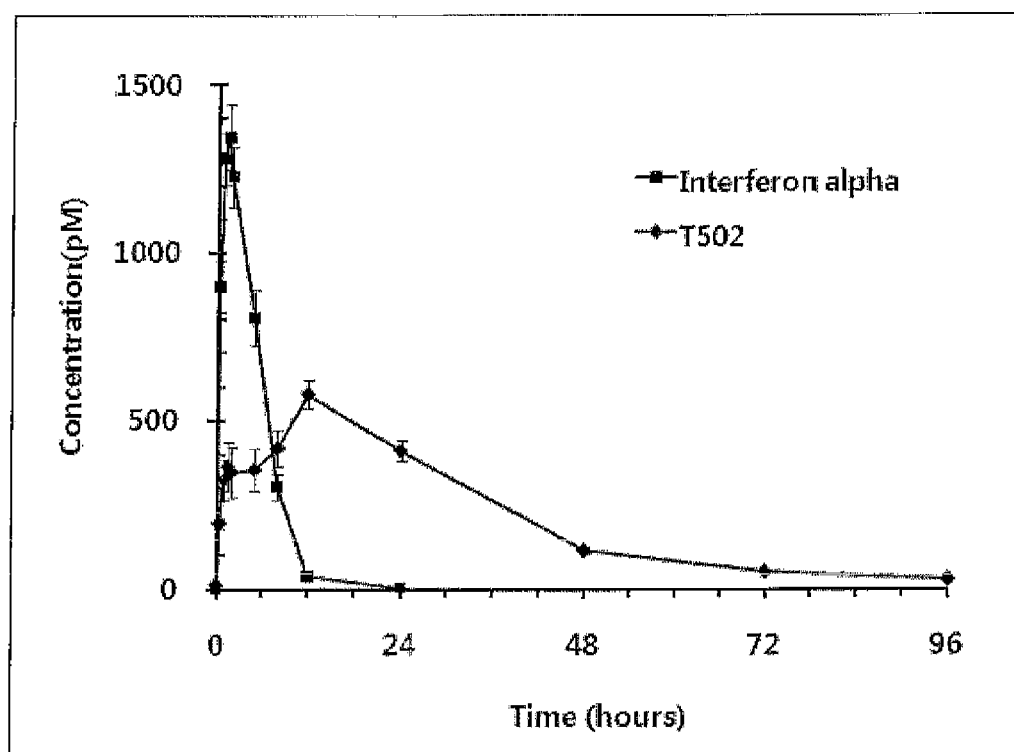
FIG. 2 is a graph demonstrating pharmacokinetic behaviors of the human interferon alpha/alpha-1 antitrypsin monovariant fusion [T502: α1AT(P357N)/IFN-α].

The pharmacokinetics of the human interferon alpha/alpha-1 antitrypsin monovariant fusion [T502: α1AT(P357N)/IFN-α] are shown in FIG. 2.

As seen in FIG. 2, the human interferon alpha/alpha-1 antitrypsin monovariant fusion [T502: α1AT(P357N)/IFN-α] had a serum half-life ($t_{1/2}$) of 18.5 hrs and a $T_{max}$ of 12 hrs while human interferon alpha had a serum half-life ($t_{1/2}$) of 3.4 hrs and a $T_{max}$ of 1.4 hrs. Thus, the human interferon alpha/alpha-1 antitrypsin monovariant fusion [T502: α1AT(P357N)/IFN-α] of the present invention is significantly increased in in vivo stability, as compared to human interferon alpha.

3. Pharmacokinetics of Granulocyte Colony-Stimulating Factor (G-CSF), Granulocyte Colony-Stimulating Factor/Alpha-1 Antitrypsin Divariant Fusion [T602S: α1AT(P357N, C232S)/G-CSF], Granulocyte Colony-Stimulating Factor/Alpha-1 Antitrypsin Trivariant Fusion[T602ST: α1AT(P357N, C232S, S359T)/G-CSF]

Sprague-Dawley rats were used as experimental animals and three of them were administered with granulocyte colony-stimulating factor while five rats were assigned to each of the fusion-administered groups. The granulocyte colony-stimulating factor/alpha-1 antitrypsin divariant fusion [T602S: α1AT(P357N, C232S)/G-CSF], and granulocyte colony-stimulating factor/alpha-1 antitrypsin trivariant fusion [T602ST: α1AT(P357N, C232S, S359T)/G-CSF], all prepared in Examples 5-6, were subcutaneously injected at a dose of 340 μg/kg into respective groups of Sprague-Dawley rats. Blood samples were taken at 0, 1, 2, 4, 8, 12, 16, 24, 30, and 48 hrs after the injection, and centrifuged to obtain sera. For a control, Filgrastim (Gracin, Jeil Pharmaceutical Co. Ltd. Korea), a commercially available granulocyte colony-stimulating factor, was subcutaneously injected at a dose of 100 μg/kg. Blood samples were taken at 0, 1, 2, 4, 8, 12, 18, 24, 30 and 48 hrs after the injection, and centrifuged to obtain sera. Each sample was analyzed in the same manner as the enzyme immunoassay of Test Example 1.

Figure 3:
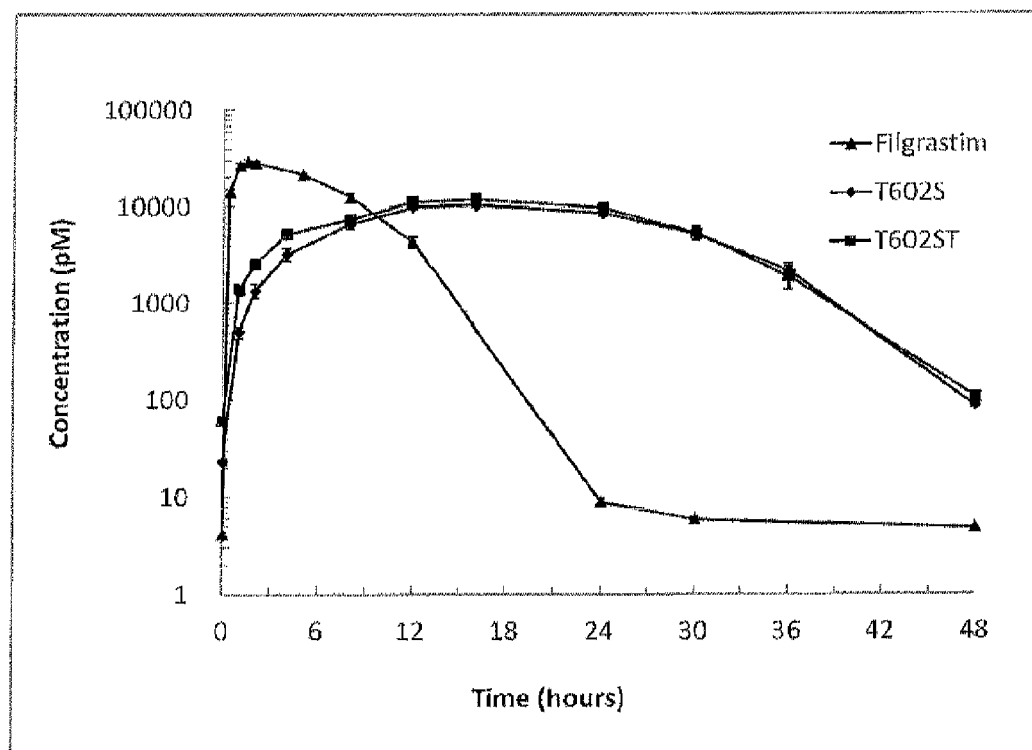
FIG. 3 is a graph demonstrating pharmacokinetic behaviors of the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT(P357N, C232S, S359T)/G-CSF].

The pharmacokinetics of the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT(P357N, C232S, S359T)/G-CSF] are depicted in FIG. 3.

As seen in FIG. 3, the granulocyte colony-stimulating factor/alpha-1 antitrypsin divariant fusion [T602S: α1AT(P357N, C232S)/G-CSF] had a serum half-life ($t_{1/2}$) of 5.1 hrs and a $T_{max}$ of 13.6 hrs and the granulocyte colony-stimulating factor/alpha-1 antitrypsin trivariant fusion[T602ST: α1AT(P357N, C232S, S359T)/G-CSF] had a serum half-life ($t_{1/2}$) of 4.5 hrs and a $T_n$ of 16 hrs. On the other hand, a serum half-life ($t_{1/2}$) of 1.8 hrs and a $T_{max}$ of 1.8 hrs were measured in the group administered with granulocyte colony-stimulating factor. Hence, the granulocyte colony-stimulating factor/alpha-1 antitrypsin divariant fusion [T602S: α1AT(P357N, C232S)/G-CSF], and the granulocyte colony-stimulating factor/alpha-1 antitrypsin trivariant fusion [T602ST: α1AT(P357N, C232S, S359T)/G-CSF] were found to have significantly increased in vivo stability, as compared to granulocyte colony-stimulating factor.

4. Pharmacokinetics of Exendin-4, Exendin-4/Alpha-1 Antitrypsin Monovariant Fusion [T304: Exendin-4/α1AT(P357N)]

Sprague-Dawley rats were used as experimental animals and five rats were assigned to each test group. The Exendin-4/alpha-1 antitrypsin monovariant fusion [T304: Exendin-4/α1AT(P357N)] prepared in Example 7 was subcutaneously injected at a dose of 520 μg/kg into Sprague-Dawley rats of each of the test groups. Blood samples were taken at 0, 1, 2, 4, 8, 12, 16, 24, 30, 48 and 72 hrs after the injection, and centrifuged to obtain sera. As a control, exendin-4 was subcutaneously injected to rats at a dose of 40 μg/kg. Blood samples were taken into heparinized tubes at 0, 10, 20, 30, 40, 60, 120, 180, 240, 300 and 360 min after the injection, and centrifuged to obtain sera. Each sample was analyzed in the same manner as the enzyme immunoassay of Test Example 1.

The pharmacokinetics of the exendin-4/alpha-1 antitrypsin monovariant fusion [T304: Exendin-4/α1AT(P357N)] are depicted in FIG. 4.

Figure 4:
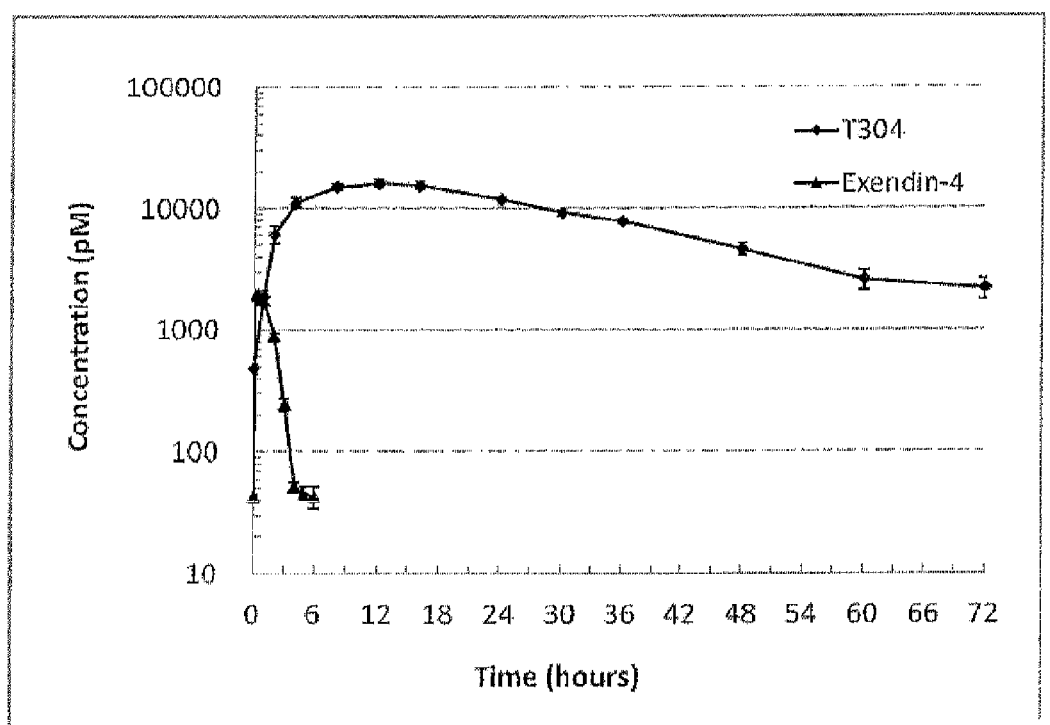
FIG. 4 is a graph demonstrating pharmacokinetic behaviors of the exendin-4/alpha-1 antitrypsin monovariant fusion [T304: Exendin-4/α1AT(P357N)].

As seen in FIG. 4, the exendin-4/alpha-1 antitrypsin monovariant fusion [T304: Exendin-4/α1AT(P357N)] had a serum half-life ($t_{1/2}$) of 19.1 hrs and a $T_{max}$ of 10.4 hrs while exendin-4 had a serum half-life ($t_{1/2}$) of 0.8 hrs and a $T_{max}$ of 0.4 hrs. Thus, the exendin-4/alpha-1 antitrypsin monovariant fusion [T304: Exendin-4/α1AT(P357N)] of the present invention has significantly increased in vivo stability, as compared to exendin-4.

Test Example 3

Assay for In Vivo Activity of the Fusion Proteins or Peptides

The following experiments were conducted to examine the in vivo activity of the fusion proteins or peptides according to the present invention.

1. In vivo Activity of Human Growth Hormone (hGH), Human Growth Hormone/Alpha-1 Antitrypsin Monovariant Fusion [T109: α1AT(P357N)/hGH]

Pituitary gland-removed Sprague-Dawley rats were used as experimental animals and divided into three groups of seven. To the hypophysectomyzed Sprague-Dawley rats, the human growth hormone/alpha-1 antitrypsin monovariant fusion [T109: α1AT(P357N)/hGH] prepared in Example 2 and human growth hormone (Eutropin, LG Life Sciences Ltd, Korea) were subcutaneously injected at doses of 18 μg and 5 μg per rat, respectively, every day. For a control, PBS was used. The rats were weighed every day after being injected.

Figure 5:
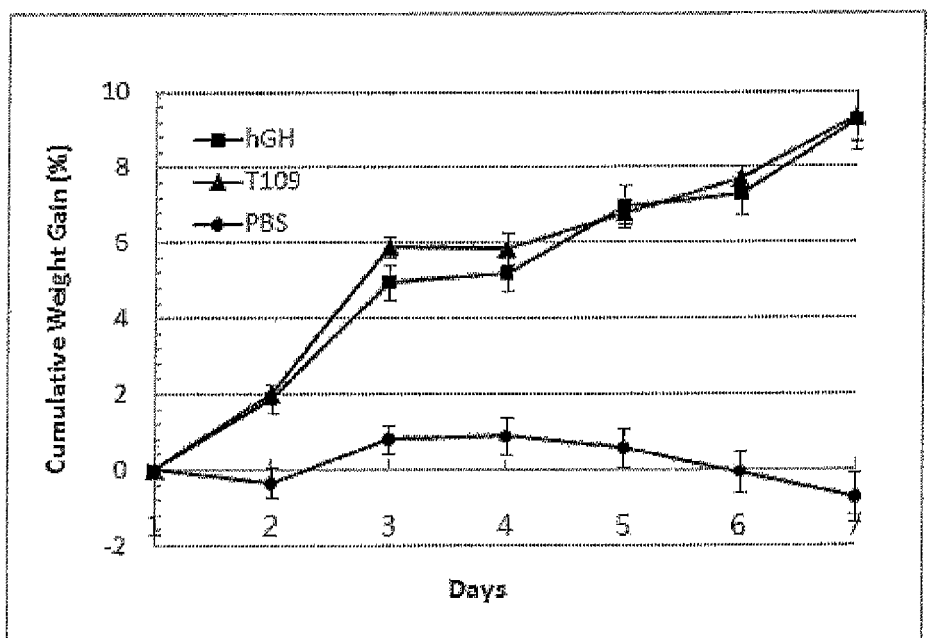
FIG. 5 is a graph showing in vivo activity (body weight change in pituitary gland-removed rats) of the human growth hormone/alpha-1 antitrypsin monovariant fusion [T109: α1AT(P357N)/hGH].

Analysis results of the in vivo activity (body weight change in pituitary gland-removed rats) of the human growth hormone/alpha-1 antitrypsin monovariant fusion [T109: α1AT(P357N)/hGH] are given in FIG. 5.

As seen in FIG. 5, the pituitary gland-removed rats gained almost no weight when administered with PBS whereas weight gain was observed by about 10.2% and 9.4% on day 7 in the pituitary gland-removed rats administered with human growth hormone and the human growth hormone/alpha-1 antitrypsin monovariant fusion [T109: α1AT(P357N)/hGH], respectively. Hence, the human growth hormone/alpha-1 antitrypsin monovariant fusion [T109: α1AT(P357N)/hGH] of the present invention was found to retain effective in vivo activity in the pituitary gland-removed rats, like human growth hormone.

2. In vivo Activity of Granulocyte Colony-Stimulating Factor (G-CSF), Granulocyte Colony-Stimulating Factor/Alpha-1 Antitrypsin Divariant Fusion [T602S: α1AT(P357N, C232S)/G-CSF], and Granulocyte Colony-Stimulating Factor/Alpha-1 Antitrypsin Trivariant Fusion [T602ST: α1AT (P357N, C232S, S3591)/G-CSF]

Sprague-Dawley rats were used as experimental animals and divided into five groups of five each. To the Sprague-Dawley rats, the granulocyte colony-stimulating factor/alpha-1 antitrypsin divariant fusion [T602S: α1AT(P357N, C232S)/G-CSF] prepared in Example 5 was subcutaneously injected at doses of 340 μg/kg and 1,700 μg/kg. To another groups of rats, the granulocyte colony-stimulating factor/alpha-1 antitrypsin trivariant fusion [T602ST: α1AT(P357N, C232S, S359T)/G-CSF] prepared in Example 6 and the granulocyte colony-stimulating factor Filgrastim (Gracin, Jell Pharmaceutical Co. Ltd. Korea) were subcutaneously injected at doses of 1,700 μg/kg and 100 μg/kg, respectively. Blood samples were taken from the tail on 3 days before experiment and on 1, 2, 3, 4 and 5 days after the injection and leucocytes were counted using Hematology Analyzer (Pentra 120).

Figure 6:
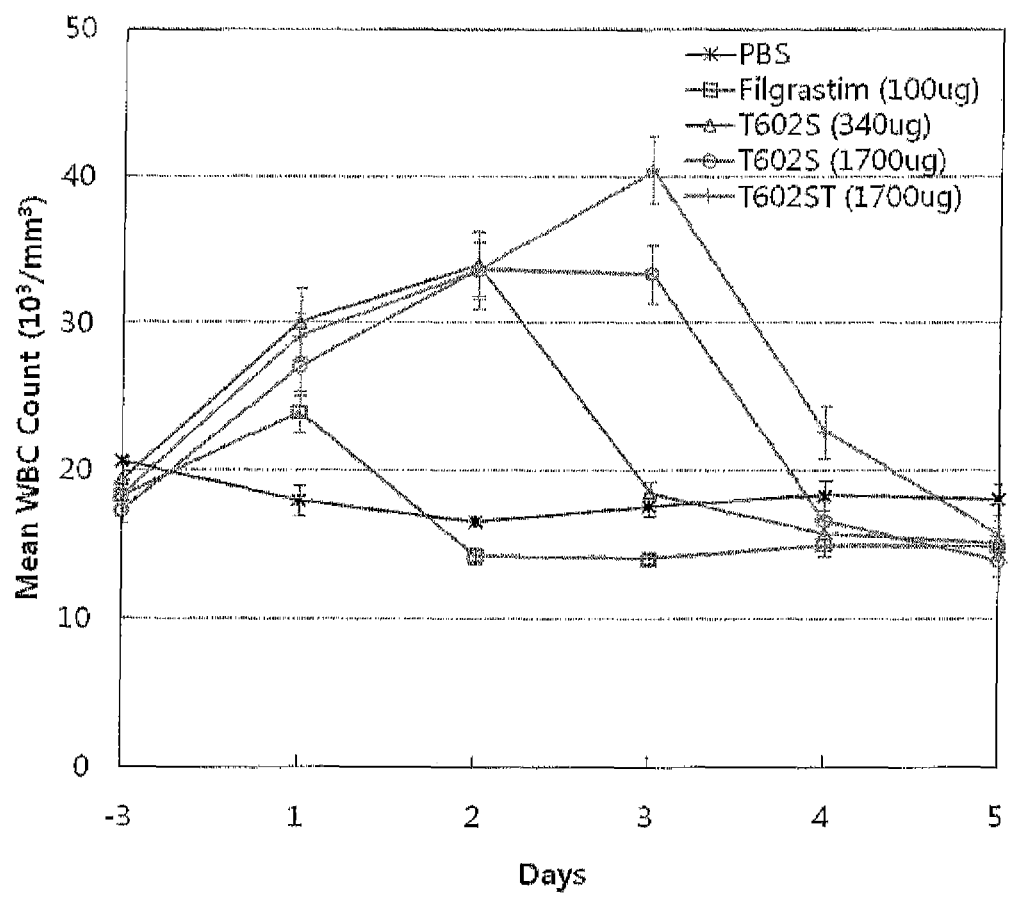
FIG. 6 is a graph showing in vivo activities (increase in leukocyte count) of the granulocyte colony-stimulating factor/alpha-1 antitrypsin divariant fusion [T602S: α1AT (P357N, C232S)/G-CSF], and the granulocyte colony-stimulating factor/alpha-1 antitrypsin trivariant fusion [T602ST: α1AT(P357N, C232S, S359I)/G-CSF].

Analysis results of the in vivo activity (changes in leucocyte level) of the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT (P357N, C232S, S359T)/G-CSF] are given in FIG. 6.

As seen in FIG. 6, the leucocyte count was observed to peak level at Day 1 and then decrease to the base line from Day 2 in the group administered with the granulocyte colony-stimulating factor Filgrastim, and peak level on Day 2 and then decrease from Day 3 in the group administered with the granulocyte colony-stimulating factor/alpha-1 antitrypsin divariant fusion [T602S: α1AT(P357N, C232S)/G-CSF] at a dose of 340 μg/kg. In the groups respectively administered with the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT(P357N, C232S, S359T)/G-CSF] at a dose of 1,700 μg/kg, the leucocyte count remained high until Day 3 and started to decrease on Day 4. Therefore, the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT(P357N, C232S, S359T)/G-CSF] were found to prolong in vivo activity over granulocyte colony-stimulating factor.

3. In vivo Activity of Exendin-4, and Exendin-4/Alpha-1 Antitrypsin Monovariant Fusion [T304: Exendin-4/α1AT (P357N)]

To examine in vivo activity of the exendin-4/alpha-1 antitrypsin monovariant fusion [T304: Exendin-4/α1AT(P357N)] of the present invention, an intraperitoneal glucose tolerance test and a blood sugar reduction test in diabetes mouse model were conducted as follows.

3-1. Intraperitoneal Glucose Tolerance Test

Eight-week-old C57BL/6 mice were fed for four weeks with high-fat feedstuff to induce obesity therein. They were starved from 15 hrs before an intraperitoneal glucose tolerance test. In this context, the exendin-4/alpha-1 antitrypsin monovariant fusion [T304: Exendin-4/α1AT (P357N)] prepared in Example 7 and exendin-4 were intraperitoneally injected once at a dose of 10 nmol/kg into the respective mouse groups, 30 min, 12 and 24 hrs after which glucose was intraperitoneally injected at a dose of 1.5 g/5 mL/kg into the mice. Blood sugar levels of the mice were measured using a glucose meter (Allmedicus, Korea) 0, 10, 20, 30, 60, 90, and 120 min after the glucose injection.

Results of the intraperitoneal glucose tolerance test with the exendin-4/alpha-1 antitrypsin monovariant fusion [T304: Exendin-4/α1AT(P357N)] are shown in FIG. 7.

Figure 7:
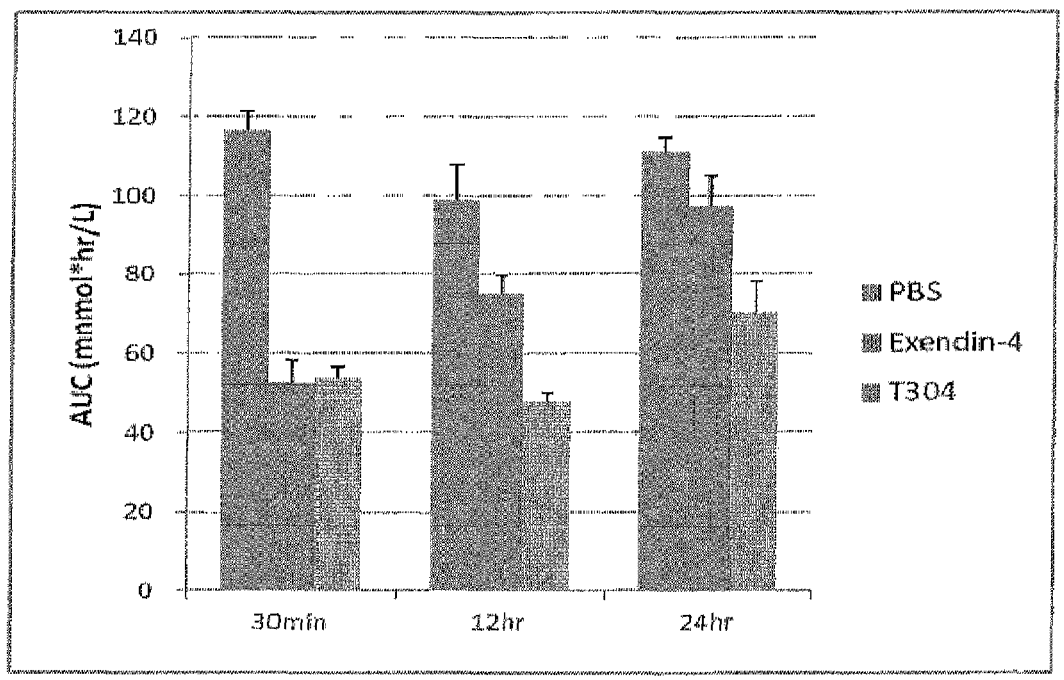
FIG. 7 is a graph showing results of an intraperitoneal glucose tolerance test conducted with exendin-4/alpha-1 antitrypsin monovariant fusion [T304: Exendin-4/α1AT (P357N)].

As seen in FIG. 7, the exendin-4/alpha-1 antitrypsin monovariant fusion [T304: Exendin-4/α1AT(P357N)] administered group maintained low glucose levels for a longer period of time than did the exendin-4-administered group.

3-2. Blood Glucose Reduction in Diabetes Mouse Model

The db/db mice, 9 weeks old, were used as experimental animals and divided of three groups of six. While being allowed to freely approach to feedstuff, the db/db mice were subcutaneously injected with the exendin-4/alpha-1 antitrypsin monovariant fusion [T304: Exendin-4/α1AT(P357N)] prepared in Example 7 or exendin-4 at a dose of 100 nmol/kg, 0, 1, 3, 6, 24, 43, 48 and 52 hrs after which blood sugar concentrations were measured using a glucose meter (Allmedicus, Korea).

The effect of the exendin-4/alpha-1 antitrypsin monovariant fusion [T304: Exendin-4/α1AT(P357N)] on the diabetes mouse model is shown in FIG. 8.

Figure 8:
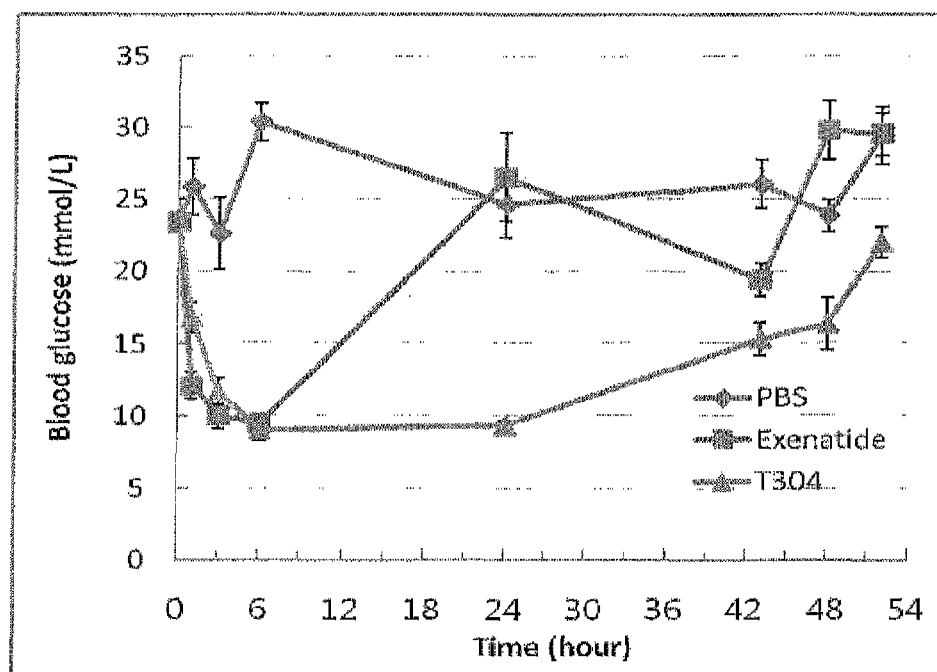
FIG. 8 is a graph showing the effect of the exendin-4/alpha-1 antitrypsin monovariant fusion [T304: Exendin-4/α1AT(P357N)] on blood sugar level in diabetes mouse models.

As seen in FIG. 8, from the time of 24 hrs after the injection, the exendin-4-administered group had blood sugar levels similar to those of the control whereas the exendin-4/alpha-1 antitrypsin monovariant fusion [T304: Exendin-4/α1AT(P357N)]-administered group maintained lower blood sugar levels, demonstrating the prolonged activity of the fusion protein.

Test Example 4

In Vitro Activity of the Fusion Proteins or Peptides

To examine the in vitro activity of the fusion proteins or peptides of the present invention, the following experiments were conducted.

1. In vitro Activity of Human Growth Hormone (hGH), Human Growth Hormone/Alpha-1 Antitrypsin Fusion [T109wt: α1AT/hGH], Human Growth Hormone/Alpha-1 Antitrypsin Monovariant Fusion [T109: α1AT(P357N)/hGH], Human Growth Hormone/Alpha-1 Antitrypsin Divariant Fusion [T109T: α1AT(P357N, S359T)/hGH]

The rat lymphoma cell line (NB2 cell) was maintained in RPMI1640 supplemented with 10% HS (Horse serum), 10% FBS, 2-mercaptoethanol and antibiotics at 37° C. under a 5% $CO_2$ condition. For 24 hrs before experiment, NB2 cells were incubated in RPMI 1640 supplemented with 10% HS. Thereafter, the NB2 cells were washed once with 1×DPBS (Dulbecco's Phosphate Buffered Saline), and plated at a density of $2 \times 10^4$ cells/100 µL/well in 5% HS-supplemented RPMI 1640 in 96-well plates (Corning, U.S.A.) with final volume of 100 µL. A series of concentrations of the samples were added in an amount of 20 µL to each well of the 96-well plates, followed by incubation at 37° C. for 48 hrs under a 5% $CO_2$ condition. Subsequently, 20 µL of an MTS solution (Promega, U.S.A.) was added to each well of the 96-well plates and allowed to react at 37° C. for 3 hrs under a 5% $CO_2$ condition. The reaction was terminated by adding 20 µL of 10% SDS (sodium dodecyl sulfate) to each well. Absorbance was measured at 490 nm using a VersaMax microplate reader (Molecular Device, U.S.A.). $EC_{50}$ (50% effective concentration) values of the drugs, that is, the concentrations at which 50% of the cells survives, were determined on the basis of the absorbance measured using the MTS method.

Figure 9:
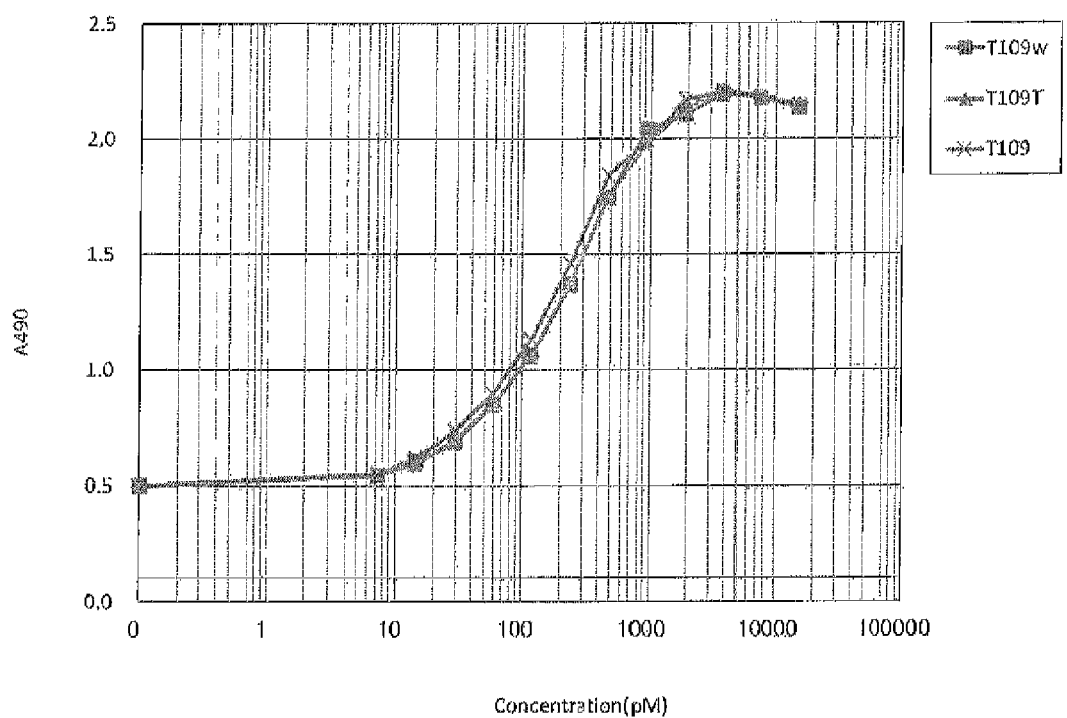
FIG. 9 is a graph showing intracellular activities of the human growth hormone/alpha-1 antitrypsin fusion [T109wt: α1AT/hGH], the human growth hormone/alpha-1 antitrypsin monovariant fusion [T109: α1AT(P357N)/hGH], and the human growth hormone/alpha-1 antitrypsin divariant fusion [T109T: α1AT (P357N, S359T)/hGH].

Analysis results of the in vitro activity of the human growth hormone/alpha-1 antitrypsin fusion [T109wt: α1AT/hGH], the human growth hormone/alpha-1 antitrypsin monovariant fusion [T109: α1AT(P357N)/hGH], and the human growth hormone/alpha-1 antitrypsin divariant fusion [T109T: α1AT(P357N, S359T)/hGH] are summarized in Table 1 and depicted in FIG. 9.

TABLE 1

| Sample | $EC_{50}$ (pM) |
|---|---|
| T109wt | 211.8 |
| T109 | 181.1 |
| T109T | 217.1 |

As is apparent from the data of Table 1 and FIG. 9, the human growth hormone/alpha-1 antitrypsin fusion [T109wt: α1AT/hGH], the human growth hormone/alpha-1 antitrypsin monovariant fusion [T109: α1AT(P357N)/hGH], and the human growth hormone/alpha-1 antitrypsin divariant fusion [T109T: α1AT(P357N, S359T)/hGH] were not significantly different in $EC_{50}$ value. Therefore, the human growth hormone/alpha-1 antitrypsin fusion [T109wt: α1AT/hGH], the human growth hormone/alpha-1 antitrypsin monovariant fusion [T109: α1AT(P357N)/hGH], and the human growth hormone/alpha-1 antitrypsin divariant fusion [T109T: α1AT(P357N, S359T)/hGH] showed relatively constant in vivo activity ($EC_{50}$) irrespective of the amino acid mutation of alpha-1 antitrypsin.

2. In vitro Activity of Granulocyte Colony-Stimulating Factor (G-CSF), Granulocyte Colony-Stimulating Factor/Alpha-1 Antitrypsin Divariant Fusion [T602S: α1AT(P357N, C232S)/G-CSF], and Granulocyte Colony-Stimulating Factor/Alpha-1 Antitrypsin Trivariant Fusion [T602ST: α1AT(P357N, C232S, S359T)/G-CSF]

Murine myeloblastic NFS-60 cells were incubated in RPMI 1640 supplemented with 10% FBS, mouse IL-3 and antibiotics at 37° C. under a 5% $CO_2$ condition. The absorbance of the cells was measured at 490 nm in the same manner as in Test Example 4-1. $EC_{50}$ (50% effective concentration) values of the drugs, that is, the concentrations at which 50% of the cells survives, were determined on the basis of the absorbance measured using the MTS method.

Figure 10:
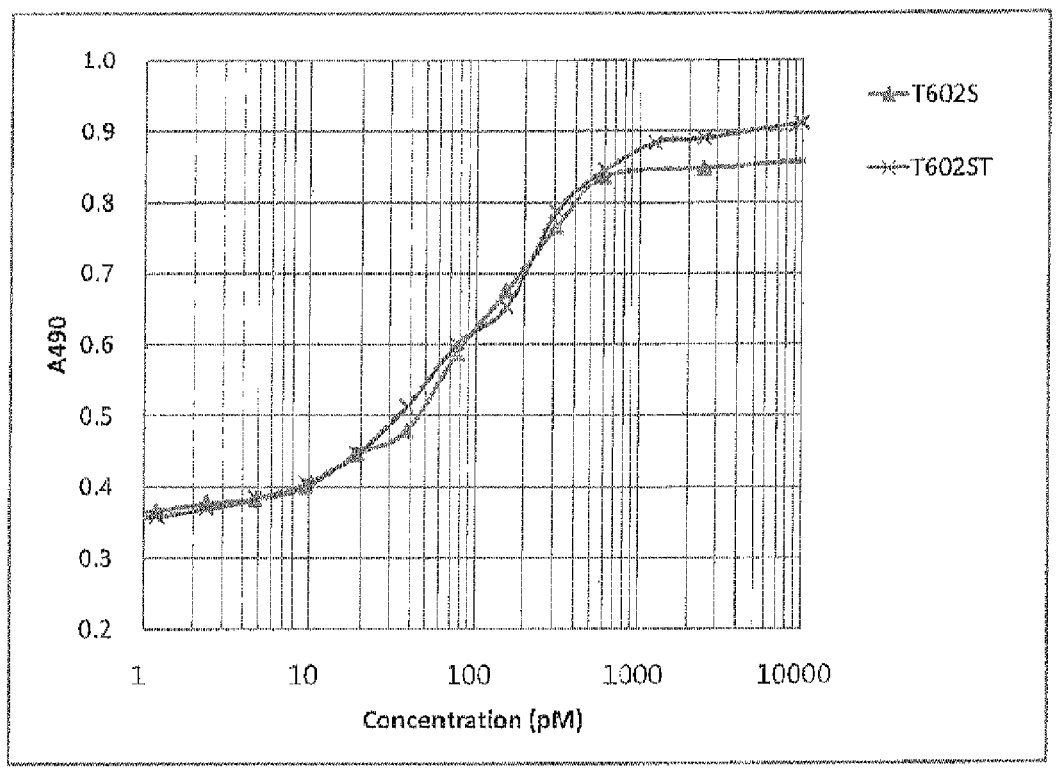
FIG. 10 is a graph showing intracellular activities of the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT (P357N, C232S, S359T)/G-CSF].

Analysis results of the in vitro activity of the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT(P357N, C232S, S359T)/G-CSF] are given in Table 2 and FIG. 10.

TABLE 2

| Sample | $EC_{50}$ (pM) |
|---|---|
| T602S | 78.1 |
| T602ST | 97.6 |

As is apparent from the data of Table 2 and FIG. 10, the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT(P357N, C232S, S359T)/G-CSF] were not significantly different in $EC_{50}$ value. Therefore, the granulocyte colony-stimulating factor/alpha-1 antitrypsin divariant fusion [T602S: α1AT(P357N, C232S)/G-CSF] and the granulocyte colony-stimulating factor/alpha-1 antitrypsin trivariant fusion [T602ST: α1AT(P357N, C232S, S359T)/G-CSF] showed relatively constant in vitro activity ($EC_{50}$) irrespective of the amino acid mutation of alpha-1 antitrypsin.

Test Example 5

Assay for Inhibitory Activity of the Fusion Proteins or Peptides Against Trypsin To examine the inhibitory activity of the human growth hormone/alpha-1 antitrypsin fusion [T109wt: α1AT/hGH] and the human growth hormone/alpha-1 antitrypsin monovariant fusion [T109: α1AT(P357N)/hGH] against trypsin, the following experiment was conducted.

The human growth hormone/alpha-1 antitrypsin fusion [T109wt: α1AT/hGH] prepared in Example 1 and the human growth hormone/alpha-1 antitrypsin monovariant fusion [T109: α1AT(P357N)/hGH] prepared in Example 1 were separately mixed with trypsin. Trypsin and the fusions were used at a concentration of 10 nM, respectively. After being incubated at room temperature for 1 hr, the mixture was reacted with 0.2 mM of the substrate N-Benzoyl-Val-Gly-Arg p-nitroanilide hydrochloride (Sigma, U.S.A.), followed by measuring absorbance at 405 nm. Trypsin unit was set to be the concentration of substrate causing a change in absorbance of 0.001 and the enzyme activity was expressed as units/mg trypsin. For comparison, trypsin was used as a control.

Figure 11:
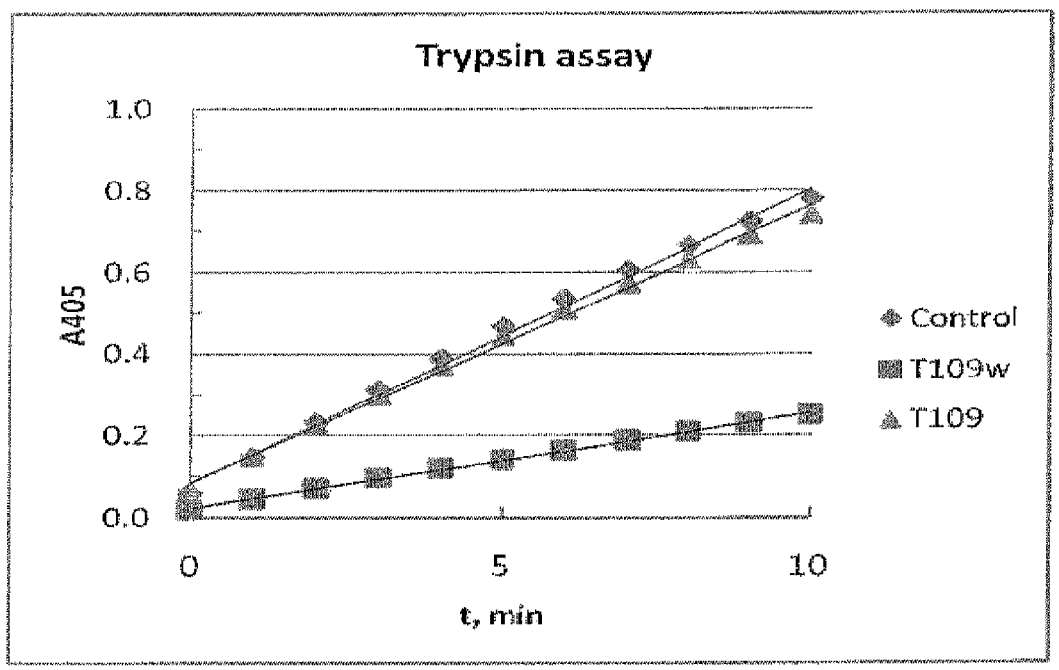
FIG. 11 is a graph showing inhibitory activities of the human growth hormone/alpha-1 antitrypsin fusion [T109wt: α1AT/hGH] and the human growth hormone/alpha-1 antitrypsin monovariant fusion [T109: α1AT(P357N)/hGH] against trypsin.

The results are depicted in FIG. 11.

As seen in FIG. 11, Ka (association equilibrium constant) between trypsin and alpha-1 antitrypsin was calculated to be about $7.5 \times 10^8$ $M^{-1}$ for the human growth hormone/alpha-1 antitrypsin fusion [T109wt: α1AT/hGH] and about $8.0 \times 10^6$ $M^{-1}$ for the human growth hormone/alpha-1 antitrypsin monovariant fusion [T109: α1AT(P357N)/hGH]. The human growth hormone/alpha-1 antitrypsin fusion [T109wt: α1AT/hGH] showed excellent inhibitory activity against trypsin whereas the human growth hormone/alpha-1 antitrypsin monovariant fusion [T109: α1AT(P357N)/hGH] was not a good trypsin inhibitor. Thus, the fact that the human growth hormone/alpha-1 antitrypsin fusion [T109wt: α1AT/hGH] and the human growth hormone/alpha-1 antitrypsin monovariant fusion [T109: α1AT(P357N)/hGH] increase in in vivo half-life by sustained circulation is not dependent on the inherent property of alpha-1 antitrypsin.

Test Example 6

Assay for Inhibitory Activity of the Fusion Proteins or Peptides Against Human Neutrophil Elastase To examine the inhibitory activity of the human growth hormone/alpha-1 antitrypsin fusion [T109wt: α1AT/hGH] and the human growth hormone/alpha-1 antitrypsin monovariant fusion [T109: α1AT(P357N)/hGH] against human neutrophil elastase, the following experiment was conducted.

The human growth hormone/alpha-1 antitrypsin fusion [T109wt: α1AT/hGH] prepared in Example 1 and the human growth hormone/alpha-1 antitrypsin monovariant fusion [T109: α1AT(P357N)/hGH] prepared in Example 1 were separately mixed with human neutrophil elastase. The elastase and the fusions were used at a concentration of 40 nM, respectively. After being incubated at room temperature for 1 hr, the mixture was reacted with 1 mM of the substrate MeOSuc-AAPV-pNA (Santa Cruz Biotechnology, Inc., U.S.A.), followed by measuring absorbance at 405 nm. Human neutrophil elastase unit was set to be the concentration of substrate causing a change in absorbance of 0.001 and the enzyme activity was expressed as units/mg elastase.

Figure 12:
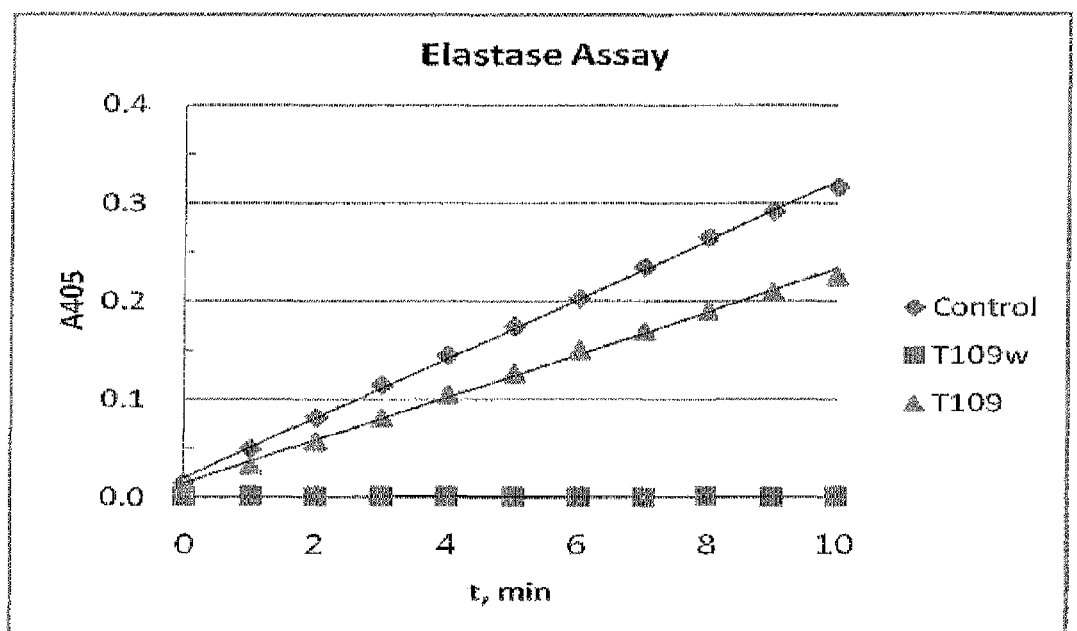
FIG. 12 is a graph showing inhibitory activities of the human growth hormone/alpha-1 antitrypsin fusion [T109wt: α1AT/hGH] and the human growth hormone/alpha-1 antitrypsin monovariant fusion [T109: α1AT(P357N)/hGH] against human neutrophil elastase.

The results are depicted in FIG. 12.

As seen in FIG. 12, the human growth hormone/alpha-1 antitrypsin fusion [T109wt: α1AT/hGH] was observed to inhibit almost 100% human neutrophil elastase while the human growth hormone/alpha-1 antitrypsin monovariant fusion [T109: α1AT(P357N)/hGH] had a Ka of about $1.4 \times 10^7 M^{-1}$. Thus, the human growth hormone/alpha-1 antitrypsin fusion [T109wt: α1AT/hGH] served as an excellent human neutrophil elastase inhibitor whereas the human growth hormone/alpha-1 antitrypsin monovariant fusion [T109: α1AT(P357N)/hGH] had low inhibitory activity against human neutrophil elastase. Therefore, the fact that the human growth hormone/alpha-1 antitrypsin fusion [T109wt: α1AT/hGH] and the human growth hormone/alpha-1 antitrypsin monovariant fusion [T109: α1AT(P357N)/hGH] increase in vivo half-life by sustained circulation is not dependent on the inherent property of alpha-1 antitrypsin.

Test Example 7

Electrophoresis Assay of the Fusion Proteins or Peptides

To examine the molecular weight change according to the addition of glycosylation site, the human growth hormone/alpha-1 antitrypsin fusion [T109wt: α1AT/hGH], the human growth hormone/alpha-1 antitrypsin monovariant fusion [T109: α1AT(P357N)/hGH] and the human growth hormone/alpha-antitrypsin divariant fusion [T109T: α1AT(P357N, S359T)/hGH] were subjected to SDS-polyacrylamide gel electrophoresis.

Figure 13:
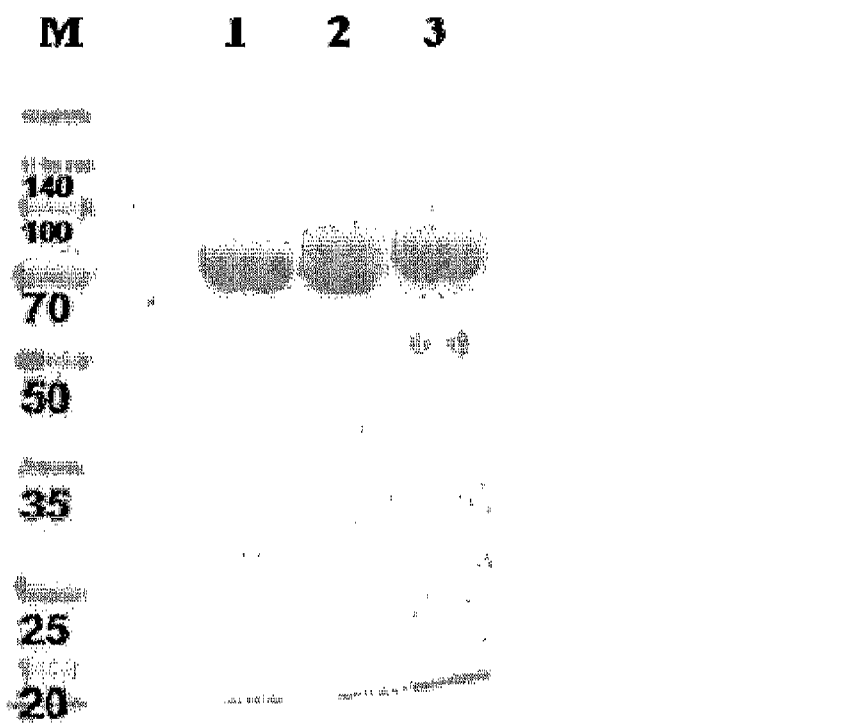
FIG. 13 is a photograph showing protein bands of the human growth hormone/alpha-1 antitrypsin fusion [T109wt: α1AT/hGH], and the human growth hormone/alpha-1 antitrypsin monovariant fusion [T109: α1AT(P357N)/hGH], and the human growth hormone/alpha-1 antitrypsin divariant fusion [T109T: α1AT(P357N, S359T)/hGH] after SDS-polyacrylamide gel electrophoresis.

The results are shown in FIG. 13.

As seen in FIG. 13, the human growth hormone/alpha-1 antitrypsin monovariant fusion [T109: α1AT(P357N)/hGH] in which an additional glycosylation site (Asn-X-Ser) was shown a protein-stained band migrated in the higher molecular weight position, as compared to the native human growth hormone/alpha-1 antitrypsin fusion [T109wt: α1AT/hGH] in which no additional glycosylation sites were generated. As for human growth hormone/alpha-1 antitrypsin divariant fusion [T109T: α1AT(P357N, S359T)/hGH], it has more extensive additional glycosylation at position 357 (Asn-X-Thr) and its increased molecular weight was even more apparent. Thus, the human growth hormone/alpha-1 antitrypsin monovariant fusion [T109: α1AT(P357N)/hGH] and the human growth hormone/alpha-1 antitrypsin divariant fusion [T109T: α1AT(P357N, S359T)/hGH] had increased molecular weights due to the addition of a glycosylation site thereto.

INDUSTRIAL APPLICABILITY

Being in sustained circulation forms, the fusion proteins or peptides of the present invention significantly increase in serum half-life ($T_{1/2}$) and show excellent in vivo stability, as compared to the physiologically active proteins or peptides themselves. Therefore, the fusion proteins or peptides of the present invention can be applied to the development of the sustained circulation dosage forms of the protein or peptide drugs.

The invention claimed is:

1. A fusion protein or peptide, comprising a physiologically active protein or peptide fused to alpha-1 antitrypsin variant having at least one mutated amino acid residue, whereby the physiologically active protein or peptide has an increased in vivo half-life by maintenance in a sustained circulation, and the alpha-1 antitrypsin variant has a reduced protease inhibitor activity, wherein the alpha-1 antitrypsin variant is selected from the group consisting of alpha-1 antitrypsin monovariant [α1AT(P357N)] set forth as SEQ ID NO:28, alpha-1 antitrypsin divariant [α1AT(P357N, S359T)] set forth as SEQ ID NO:29, alpha-1 antitrypsin divariant [α1AT(P357N, C232S)] set forth as SEQ ID NO:30, and alpha-1 antitrypsin trivariant α1AT(P357N, C232S, S359T) set forth as SEQ ID NO:31.

2. The fusion protein or peptide of claim 1, wherein the physiologically active protein or peptide is fused directly or via a linker consisting of amino acids to alpha-1 antitrypsin variant having at least one mutated amino acid residue.

3. The fusion protein or peptide of claim 1, wherein the physiologically active protein is selected from the group consisting of hormones and their receptors, biological response modifiers and their receptors, cytokines and their receptors, enzymes, antibodies, and antibody fragments.

4. The fusion protein or peptide of claim 3, wherein the physiologically active protein is selected from the group consisting of human growth hormone (hGH), insulin, follicle-stimulating hormone (FSH), human chorionic gonadotropin, parathyroid hormone (PTH), erythropoietin (EPO), thrombopoietin (TPO), granulocyte colony-stimulating factor (G-CSF), granulocyte macrophage colony-stimulating factor (GM-CSF), interferon alpha, interferon beta, interferon gamma, interleukins, macrophage activating factor, tumor necrosis factor, tissue plasminogen activator, coagulation factor VII, VIIa, VIII and IX, human bone morphogenic protein 2 (hBMP2), keratinocyte growth factor (KGF), platelet-derived growth factor (PDGF), glucocerebrosidase, α-galactosidase A, α-L-iduronidase, iduronate-2-sulfatase, lactase, adenosine deaminase, butyrylcholinesterase, chitinase, glutamate decarboxylase, imiglucerase, lipase, uricase, platelet-activating factor acetylhydrolase, neutral endopeptidase, urokinase, streptokinase, myeloperoxidase, superoxide dismutase, botulinum toxin, collagenase, hyaluronidase, L-asparaginase, monoclonal antibodies, polyclonal antibodies, scFv, Fab, Fab', F(ab')$_2$ and Fd, and a combination thereof.

5. The fusion protein or peptide of claim 1, being selected from the group consisting of a human growth hormone/alpha-1 antitrypsin monovariant fusion [T109: α1AT(P357N)/hGH](SEQ ID NO: 2), a human growth hormone/alpha-1 antitrypsin divariant fusion [T109T: α1AT(P357N, S359T)/hGH](SEQ ID NO: 3), a human interferon alpha/alpha-1 antitrypsin monovariant fusion [T502: α1AT(P357N)/IFN-α](SEQ ID NO: 4), a granulocyte colony-stimulating factor/alpha-1 antitrypsin divariant fusion [T602S: α1AT(P357N, C232S)/G-CSF] (SEQ ID NO: 5), a granulocyte colony-stimulating factor/alpha-1 antitrypsin trivariant fusion [T602ST: α1AT(P357N, C232S, S359T)/G-CSF] (SEQ ID NO: 6), and an exendin-4/alpha-1 antitrypsin monovariant fusion [T304: Exendin-4/α1AT(P357N)](SEQ ID NO: 7).

* * * * *

SEQUENCE LISTING

<160> NUMBER OF SEQ ID NOS: 32

<210> SEQ ID NO 1
<211> LENGTH: 590
<212> TYPE: PRT
<213> ORGANISM: Artificial Sequence
<220> FEATURE:
<223> OTHER INFORMATION: T109wt(alpha-1AT/hGH)

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys Gly Gly Gly Gly Ser Phe
385                 390                 395                 400

```
Pro Thr Ile Pro Leu Ser Arg Leu Phe Asp Asn Ala Met Leu Arg Ala
                405                 410                 415

His Arg Leu His Gln Leu Ala Phe Asp Thr Tyr Gln Glu Phe Glu Glu
            420                 425                 430

Ala Tyr Ile Pro Lys Glu Gln Lys Tyr Ser Phe Leu Gln Asn Pro Gln
            435                 440                 445

Thr Ser Leu Cys Phe Ser Glu Ser Ile Pro Thr Pro Ser Asn Arg Glu
        450                 455                 460

Glu Thr Gln Gln Lys Ser Asn Leu Glu Leu Leu Arg Ile Ser Leu Leu
465                 470                 475                 480

Leu Ile Gln Ser Trp Leu Glu Pro Val Gln Phe Leu Arg Ser Val Phe
                485                 490                 495

Ala Asn Ser Leu Val Tyr Gly Ala Ser Asp Ser Asn Val Tyr Asp Leu
            500                 505                 510

Leu Lys Asp Leu Glu Glu Gly Ile Gln Thr Leu Met Gly Arg Leu Glu
        515                 520                 525

Asp Gly Ser Pro Arg Thr Gly Gln Ile Phe Lys Gln Thr Tyr Ser Lys
        530                 535                 540

Phe Asp Thr Asn Ser His Asn Asp Asp Ala Leu Leu Lys Asn Tyr Gly
545                 550                 555                 560

Leu Leu Tyr Cys Phe Arg Lys Asp Met Asp Lys Val Glu Thr Phe Leu
                565                 570                 575

Arg Ile Val Gln Cys Arg Ser Val Glu Gly Ser Cys Gly Phe
                580                 585                 590

<210> SEQ ID NO 2
<211> LENGTH: 590
<212> TYPE: PRT
<213> ORGANISM: Artificial Sequence
<220> FEATURE:
<223> OTHER INFORMATION: T109 [alpha-1AT(P357N)/hGH]

<400> SEQUENCE: 2

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175
```

```
Asp Arg Asp Thr Val Phe Ala Leu Val Asn Tyr Ile Phe Phe Lys Gly
            180                 185                 190
Lys Trp Glu Arg Pro Phe Glu Val Lys Asp Thr Glu Glu Asp Phe
        195                 200                 205
His Val Asp Gln Val Thr Thr Val Lys Val Pro Met Met Lys Arg Leu
    210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
    290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Ala Ile Asn Met Ser Ile Pro Pro Glu Val Lys Phe Asn Lys
        355                 360                 365
Pro Phe Val Phe Leu Met Ile Asp Gln Asn Thr Lys Ser Pro Leu Phe
    370                 375                 380
Met Gly Lys Val Val Asn Pro Thr Gln Lys Gly Gly Gly Ser Phe
385                 390                 395                 400
Pro Thr Ile Pro Leu Ser Arg Leu Phe Asp Asn Ala Met Leu Arg Ala
                405                 410                 415
His Arg Leu His Gln Leu Ala Phe Asp Thr Tyr Gln Glu Phe Glu Glu
            420                 425                 430
Ala Tyr Ile Pro Lys Glu Gln Lys Tyr Ser Phe Leu Gln Asn Pro Gln
        435                 440                 445
Thr Ser Leu Cys Phe Ser Glu Ser Ile Pro Thr Pro Ser Asn Arg Glu
    450                 455                 460
Glu Thr Gln Gln Lys Ser Asn Leu Glu Leu Leu Arg Ile Ser Leu Leu
465                 470                 475                 480
Leu Ile Gln Ser Trp Leu Glu Pro Val Gln Phe Leu Arg Ser Val Phe
                485                 490                 495
Ala Asn Ser Leu Val Tyr Gly Ala Ser Asp Ser Asn Val Tyr Asp Leu
            500                 505                 510
Leu Lys Asp Leu Glu Glu Gly Ile Gln Thr Leu Met Gly Arg Leu Glu
        515                 520                 525
Asp Gly Ser Pro Arg Thr Gly Gln Ile Phe Lys Gln Thr Tyr Ser Lys
    530                 535                 540
Phe Asp Thr Asn Ser His Asn Asp Asp Ala Leu Leu Lys Asn Tyr Gly
545                 550                 555                 560
Leu Leu Tyr Cys Phe Arg Lys Asp Met Asp Lys Val Glu Thr Phe Leu
                565                 570                 575
Arg Ile Val Gln Cys Arg Ser Val Glu Gly Ser Cys Gly Phe
            580                 585                 590
```

<210> SEQ ID NO 3
<211> LENGTH: 590
<212> TYPE: PRT
<213> ORGANISM: Artificial Sequence
<220> FEATURE:
<223> OTHER INFORMATION: T109T [alpha-1AT(P357N, S359T)/hGH]

<400> SEQUENCE: 3

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Asn Met Thr Ile Pro Pro Glu Val Lys Phe Asn Lys
        355                 360                 365
```

Pro Phe Val Phe Leu Met Ile Asp Gln Asn Thr Lys Ser Pro Leu Phe
            370                 375                 380

Met Gly Lys Val Val Asn Pro Thr Gln Lys Gly Gly Gly Ser Phe
385                 390                 395                 400

Pro Thr Ile Pro Leu Ser Arg Leu Phe Asp Asn Ala Met Leu Arg Ala
                405                 410                 415

His Arg Leu His Gln Leu Ala Phe Asp Thr Tyr Gln Glu Phe Glu Glu
                420                 425                 430

Ala Tyr Ile Pro Lys Glu Gln Lys Tyr Ser Phe Leu Gln Asn Pro Gln
                435                 440                 445

Thr Ser Leu Cys Phe Ser Glu Ser Ile Pro Thr Pro Ser Asn Arg Glu
450                 455                 460

Glu Thr Gln Gln Lys Ser Asn Leu Glu Leu Leu Arg Ile Ser Leu Leu
465                 470                 475                 480

Leu Ile Gln Ser Trp Leu Glu Pro Val Gln Phe Leu Arg Ser Val Phe
                485                 490                 495

Ala Asn Ser Leu Val Tyr Gly Ala Ser Asp Ser Asn Val Tyr Asp Leu
                500                 505                 510

Leu Lys Asp Leu Glu Glu Gly Ile Gln Thr Leu Met Gly Arg Leu Glu
                515                 520                 525

Asp Gly Ser Pro Arg Thr Gly Gln Ile Phe Lys Gln Thr Tyr Ser Lys
                535                 540

Phe Asp Thr Asn Ser His Asn Asp Asp Ala Leu Leu Lys Asn Tyr Gly
545                 550                 555                 560

Leu Leu Tyr Cys Phe Arg Lys Asp Met Asp Lys Val Glu Thr Phe Leu
                565                 570                 575

Arg Ile Val Gln Cys Arg Ser Val Glu Gly Ser Cys Gly Phe
                580                 585                 590

<210> SEQ ID NO 4
<211> LENGTH: 564
<212> TYPE: PRT
<213> ORGANISM: Artificial Sequence
<220> FEATURE:
<223> OTHER INFORMATION: T502 [alpha-1AT(P357N)/IFN-alpha]

<400> SEQUENCE: 4

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

-continued

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
        165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
        210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
        340                 345                 350

Leu Glu Ala Ile Asn Met Ser Ile Pro Pro Glu Val Lys Phe Asn Lys
            355                 360                 365

Pro Phe Val Phe Leu Met Ile Asp Gln Asn Thr Lys Ser Pro Leu Phe
        370                 375                 380

Met Gly Lys Val Val Asn Pro Thr Gln Lys Gly Gly Gly Ser Cys
385                 390                 395                 400

Asp Leu Pro Gln Thr His Ser Leu Gly Ser Arg Arg Thr Leu Met Leu
            405                 410                 415

Leu Ala Gln Met Arg Arg Ile Ser Leu Phe Ser Cys Leu Lys Asp Arg
        420                 425                 430

His Asp Phe Gly Phe Pro Gln Glu Glu Phe Gly Asn Gln Phe Gln Lys
        435                 440                 445

Ala Glu Thr Ile Pro Val Leu His Glu Met Ile Gln Gln Ile Phe Asn
    450                 455                 460

Leu Phe Ser Thr Lys Asp Ser Ser Ala Ala Trp Asp Glu Thr Leu Leu
465                 470                 475                 480

Asp Lys Phe Tyr Thr Glu Leu Tyr Gln Gln Leu Asn Asp Leu Glu Ala
            485                 490                 495

Cys Val Ile Gln Gly Val Gly Val Thr Glu Thr Pro Leu Met Lys Glu
        500                 505                 510

Asp Ser Ile Leu Ala Val Arg Lys Tyr Phe Gln Arg Ile Thr Leu Tyr
        515                 520                 525

Leu Lys Glu Lys Lys Tyr Ser Pro Cys Ala Trp Glu Val Val Arg Ala
    530                 535                 540

Glu Ile Met Arg Ser Phe Ser Leu Ser Thr Asn Leu Gln Glu Ser Leu
545                 550                 555                 560

Arg Ser Lys Glu

<210> SEQ ID NO 5
<211> LENGTH: 573
<212> TYPE: PRT
<213> ORGANISM: Artificial Sequence
<220> FEATURE:
<223> OTHER INFORMATION: T602S [alpha-1AT(P357N, C232S)/G-CSF]

<400> SEQUENCE: 5

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Ser Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Asn Met Ser Ile Pro Pro Glu Val Lys Phe Asn Lys
        355                 360                 365
```

```
Pro Phe Val Phe Leu Met Ile Asp Gln Asn Thr Lys Ser Pro Leu Phe
    370                 375                 380

Met Gly Lys Val Val Asn Pro Thr Gln Lys Gly Gly Gly Ser Thr
385                 390                 395                 400

Pro Leu Gly Pro Ala Ser Ser Leu Pro Gln Ser Phe Leu Leu Lys Cys
                405                 410                 415

Leu Glu Gln Val Arg Lys Ile Gln Gly Asp Gly Ala Ala Leu Gln Glu
            420                 425                 430

Lys Leu Cys Ala Thr Tyr Lys Leu Cys His Pro Glu Glu Leu Val Leu
            435                 440                 445

Leu Gly His Ser Leu Gly Ile Pro Trp Ala Pro Leu Ser Ser Cys Pro
450                 455                 460

Ser Gln Ala Leu Gln Leu Ala Gly Cys Leu Ser Gln Leu His Ser Gly
465                 470                 475                 480

Leu Phe Leu Tyr Gln Gly Leu Leu Gln Ala Leu Glu Gly Ile Ser Pro
                485                 490                 495

Glu Leu Gly Pro Thr Leu Asp Thr Leu Gln Leu Asp Val Ala Asp Phe
                500                 505                 510

Ala Thr Thr Ile Trp Gln Gln Met Glu Glu Leu Gly Met Ala Pro Ala
            515                 520                 525

Leu Gln Pro Thr Gln Gly Ala Met Pro Ala Phe Ala Ser Ala Phe Gln
            530                 535                 540

Arg Arg Ala Gly Gly Val Leu Val Ala Ser His Leu Gln Ser Phe Leu
545                 550                 555                 560

Glu Val Ser Tyr Arg Val Leu Arg His Leu Ala Gln Pro
                565                 570

<210> SEQ ID NO 6
<211> LENGTH: 573
<212> TYPE: PRT
<213> ORGANISM: Artificial Sequence
<220> FEATURE:
<223> OTHER INFORMATION: T602ST [alpha-1AT(P357N, C232S, S359T)/G-CSF]

<400> SEQUENCE: 6

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160
```

-continued

Val Glu Lys Gly Thr Gln Gly Lys Ile Val Asp Leu Val Lys Glu Leu
              165                 170                 175

Asp Arg Asp Thr Val Phe Ala Leu Val Asn Tyr Ile Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Ser Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Asn Met Thr Ile Pro Pro Glu Val Lys Phe Asn Lys
        355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys Gly Gly Gly Ser Thr
385                 390                 395                 400

Pro Leu Gly Pro Ala Ser Ser Leu Pro Gln Ser Phe Leu Leu Lys Cys
                405                 410                 415

Leu Glu Gln Val Arg Lys Ile Gln Gly Asp Gly Ala Ala Leu Gln Glu
            420                 425                 430

Lys Leu Cys Ala Thr Tyr Lys Leu Cys His Pro Glu Glu Leu Val Leu
        435                 440                 445

Leu Gly His Ser Leu Gly Ile Pro Trp Ala Pro Leu Ser Ser Cys Pro
    450                 455                 460

Ser Gln Ala Leu Gln Leu Ala Gly Cys Leu Ser Gln Leu His Ser Gly
465                 470                 475                 480

Leu Phe Leu Tyr Gln Gly Leu Leu Gln Ala Leu Glu Gly Ile Ser Pro
                485                 490                 495

Glu Leu Gly Pro Thr Leu Asp Thr Leu Gln Leu Asp Val Ala Asp Phe
            500                 505                 510

Ala Thr Thr Ile Trp Gln Gln Met Glu Glu Leu Gly Met Ala Pro Ala
        515                 520                 525

Leu Gln Pro Thr Gln Gly Ala Met Pro Ala Phe Ala Ser Ala Phe Gln
    530                 535                 540

Arg Arg Ala Gly Gly Val Leu Val Ala Ser His Leu Gln Ser Phe Leu
545                 550                 555                 560

Glu Val Ser Tyr Arg Val Leu Arg His Leu Ala Gln Pro
                565                 570

```
<210> SEQ ID NO 7
<211> LENGTH: 433
<212> TYPE: PRT
<213> ORGANISM: Artificial Sequence
<220> FEATURE:
<223> OTHER INFORMATION: T304 [Exendin-4/alpha-1AT(P357N)]

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Glu Asp Pro Gln Gly Asp Ala Ala Gln
        35                  40                  45

Lys Thr Asp Thr Ser His His Asp Gln Asp His Pro Thr Phe Asn Lys
50                  55                  60

Ile Thr Pro Asn Leu Ala Glu Phe Ala Phe Ser Leu Tyr Arg Gln Leu
65                  70                  75                  80

Ala His Gln Ser Asn Ser Thr Asn Ile Phe Phe Ser Pro Val Ser Ile
                85                  90                  95

Ala Thr Ala Phe Ala Met Leu Ser Leu Gly Thr Lys Ala Asp Thr His
            100                 105                 110

Asp Glu Ile Leu Glu Gly Leu Asn Phe Asn Leu Thr Glu Ile Pro Glu
        115                 120                 125

Ala Gln Ile His Glu Gly Phe Gln Glu Leu Leu His Thr Leu Asn Gln
130                 135                 140

Pro Asp Ser Gln Leu Gln Leu Thr Thr Gly Asn Gly Leu Phe Leu Ser
145                 150                 155                 160

Glu Gly Leu Lys Leu Val Asp Lys Phe Leu Glu Asp Val Lys Lys Leu
                165                 170                 175

Tyr His Ser Glu Ala Phe Thr Val Asn Phe Gly Asp Thr Glu Glu Ala
            180                 185                 190

Lys Lys Gln Ile Asn Asp Tyr Val Glu Lys Gly Thr Gln Gly Lys Ile
        195                 200                 205

Val Asp Leu Val Lys Glu Leu Asp Arg Asp Thr Val Phe Ala Leu Val
210                 215                 220

Asn Tyr Ile Phe Phe Lys Gly Lys Trp Glu Arg Pro Phe Glu Val Lys
225                 230                 235                 240

Asp Thr Glu Glu Glu Asp Phe His Val Asp Gln Val Thr Thr Val Lys
                245                 250                 255

Val Pro Met Met Lys Arg Leu Gly Met Phe Asn Ile Gln His Cys Lys
            260                 265                 270

Lys Leu Ser Ser Trp Val Leu Leu Met Lys Tyr Leu Gly Asn Ala Thr
        275                 280                 285

Ala Ile Phe Phe Leu Pro Asp Glu Gly Lys Leu Gln His Leu Glu Asn
290                 295                 300

Glu Leu Thr His Asp Ile Ile Thr Lys Phe Leu Glu Asn Glu Asp Arg
305                 310                 315                 320

Arg Ser Ala Ser Leu His Leu Pro Lys Leu Ser Ile Thr Gly Thr Tyr
                325                 330                 335

Asp Leu Lys Ser Val Leu Gly Gln Leu Gly Ile Thr Lys Val Phe Ser
            340                 345                 350

Asn Gly Ala Asp Leu Ser Gly Val Thr Glu Glu Ala Pro Leu Lys Leu
        355                 360                 365
```

```
Ser Lys Ala Val His Lys Ala Val Leu Thr Ile Asp Glu Lys Gly Thr
370                 375                 380

Glu Ala Ala Gly Ala Met Phe Leu Glu Ala Ile Asn Met Ser Ile Pro
385                 390                 395                 400

Pro Glu Val Lys Phe Asn Lys Pro Phe Val Phe Leu Met Ile Asp Gln
                405                 410                 415

Asn Thr Lys Ser Pro Leu Phe Met Gly Lys Val Val Asn Pro Thr Gln
                420                 425                 430

Lys
```

<210> SEQ ID NO 8
<211> LENGTH: 30
<212> TYPE: DNA
<213> ORGANISM: Artificial Sequence
<220> FEATURE:
<223> OTHER INFORMATION: primer (ALT21)

<400> SEQUENCE: 8
ccctcctcga gaatgccgtc ttctgtctcg                                30

<210> SEQ ID NO 9
<211> LENGTH: 36
<212> TYPE: DNA
<213> ORGANISM: Artificial Sequence
<220> FEATURE:
<223> OTHER INFORMATION: primer (ALT30)

<400> SEQUENCE: 9
gggcccggat cctcctcctc cttttgggt gggatt                          36

<210> SEQ ID NO 10
<211> LENGTH: 26
<212> TYPE: DNA
<213> ORGANISM: Artificial Sequence
<220> FEATURE:
<223> OTHER INFORMATION: primer (DH22)

<400> SEQUENCE: 10
ggatccttcc caaccattcc cttatc                                    26

<210> SEQ ID NO 11
<211> LENGTH: 30
<212> TYPE: DNA
<213> ORGANISM: Artificial Sequence
<220> FEATURE:
<223> OTHER INFORMATION: primer (ALT12)

<400> SEQUENCE: 11
gggggcggcc gcctagaagc cacagctgcc                                30

<210> SEQ ID NO 12
<211> LENGTH: 38
<212> TYPE: DNA
<213> ORGANISM: Artificial Sequence
<220> FEATURE:
<223> OTHER INFORMATION: primer (ALT1)

<400> SEQUENCE: 12
ccatgttttt agaggccata aacatgtcta tccccccc                       38

<210> SEQ ID NO 13
<211> LENGTH: 38
<212> TYPE: DNA
<213> ORGANISM: Artificial Sequence

```
<220> FEATURE:
<223> OTHER INFORMATION: primer (ALT2)

<400> SEQUENCE: 13
gggggggata gacatgttta tggcctctaa aaacatgg                               38

<210> SEQ ID NO 14
<211> LENGTH: 32
<212> TYPE: DNA
<213> ORGANISM: Artificial Sequence
<220> FEATURE:
<223> OTHER INFORMATION: primer (ALT14)

<400> SEQUENCE: 14
gggcccctcg aggaagatcc ccagggagat gc                                     32

<210> SEQ ID NO 15
<211> LENGTH: 33
<212> TYPE: DNA
<213> ORGANISM: Artificial Sequence
<220> FEATURE:
<223> OTHER INFORMATION: primer (ALT82)

<400> SEQUENCE: 15
actatccccc ccgaggtcaa gttcaacaaa ccc                                    33

<210> SEQ ID NO 16
<211> LENGTH: 27
<212> TYPE: DNA
<213> ORGANISM: Artificial Sequence
<220> FEATURE:
<223> OTHER INFORMATION: primer (ALT83)

<400> SEQUENCE: 16
catgtttatg gcctctaaaa acatggc                                           27

<210> SEQ ID NO 17
<211> LENGTH: 30
<212> TYPE: DNA
<213> ORGANISM: Artificial Sequence
<220> FEATURE:
<223> OTHER INFORMATION: primer (ALT45)

<400> SEQUENCE: 17
gggcccggat cctgtgatct gcctcaaacc                                        30

<210> SEQ ID NO 18
<211> LENGTH: 30
<212> TYPE: DNA
<213> ORGANISM: Artificial Sequence
<220> FEATURE:
<223> OTHER INFORMATION: primer (ALT49)

<400> SEQUENCE: 18
gcgggcggcc gctcattcct tacttcttaa                                        30

<210> SEQ ID NO 19
<211> LENGTH: 38
<212> TYPE: DNA
<213> ORGANISM: Artificial Sequence
<220> FEATURE:
<223> OTHER INFORMATION: primer (ALT52)

<400> SEQUENCE: 19
gcatgtttaa catccagcac tctaagaagc tgtccagc                               38
```

<210> SEQ ID NO 20
<211> LENGTH: 38
<212> TYPE: DNA
<213> ORGANISM: Artificial Sequence
<220> FEATURE:
<223> OTHER INFORMATION: primer (ALT53)

<400> SEQUENCE: 20
gctggacagc ttcttagagt gctggatgtt aaacatgc            38

<210> SEQ ID NO 21
<211> LENGTH: 30
<212> TYPE: DNA
<213> ORGANISM: Artificial Sequence
<220> FEATURE:
<223> OTHER INFORMATION: primer (ALT56)

<400> SEQUENCE: 21
gggcccggat ccacccccct gggccctgcc            30

<210> SEQ ID NO 22
<211> LENGTH: 30
<212> TYPE: DNA
<213> ORGANISM: Artificial Sequence
<220> FEATURE:
<223> OTHER INFORMATION: primer (ALT57)

<400> SEQUENCE: 22
gcgggcggcc gctcagggct gggcaaggtg            30

<210> SEQ ID NO 23
<211> LENGTH: 31
<212> TYPE: DNA
<213> ORGANISM: Artificial Sequence
<220> FEATURE:
<223> OTHER INFORMATION: primer (ALT5)

<400> SEQUENCE: 23
gggcccgcgg ccgcagttat ttttgggtgg g            31

<210> SEQ ID NO 24
<211> LENGTH: 145
<212> TYPE: DNA
<213> ORGANISM: Artificial Sequence
<220> FEATURE:
<223> OTHER INFORMATION: primer (DH15)

<400> SEQUENCE: 24
ggatccgacg atgacgataa gcatggcgaa ggaacattca ccagcgactt gtcaaaacag            60
atggaagagg aggcagtgcg gttatttatt gagtggctta agaacggcgg accaagtagc            120
ggggcacctc cgccatctgc tagca            145

<210> SEQ ID NO 25
<211> LENGTH: 145
<212> TYPE: DNA
<213> ORGANISM: Artificial Sequence
<220> FEATURE:
<223> OTHER INFORMATION: primer (DH16)

<400> SEQUENCE: 25
gctagcagat ggcggaggtg ccccgctact tggtccgccg ttcttaagcc actcaataaa            60
taaccgcact gcctcctctt ccatctgttt tgacaagtcg ctggtgaatg ttccttcgcc            120
atgcttatcg tcatcgtcgg atcca            145

<210> SEQ ID NO 26
<211> LENGTH: 108
<212> TYPE: DNA
<213> ORGANISM: Artificial Sequence
<220> FEATURE:
<223> OTHER INFORMATION: primer (ALT44)

<400> SEQUENCE: 26
gggcccctcg agatggctac aggctcccgg acgtccctgc tcctggcttt tggcctgctc    60
tgcctgccct ggcttcaaga gggcagtgcc catggcgaag gaacattc                108

<210> SEQ ID NO 27
<211> LENGTH: 30
<212> TYPE: DNA
<213> ORGANISM: Artificial Sequence
<220> FEATURE:
<223> OTHER INFORMATION: primer (ALT41)

<400> SEQUENCE: 27 gggggggatcc tcagatggcg gaggtgcccc                                    30

<210> SEQ ID NO 28
<211> LENGTH: 394
<212> TYPE: PRT
<213> ORGANISM: Artificial Sequence
<220> FEATURE:
<223> OTHER INFORMATION: Alpha-1 antitrypsin variant portion of fusion
      protein

<400> SEQUENCE: 28

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

```
Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
        340                 345                 350

Leu Glu Ala Ile Asn Met Ser Ile Pro Pro Glu Val Lys Phe Asn Lys
    355                 360                 365

Pro Phe Val Phe Leu Met Ile Asp Gln Asn Thr Lys Ser Pro Leu Phe
370                 375                 380

Met Gly Lys Val Val Asn Pro Thr Gln Lys
385                 390

<210> SEQ ID NO 29
<211> LENGTH: 394
<212> TYPE: PRT
<213> ORGANISM: Artificial Sequence
<220> FEATURE:
<223> OTHER INFORMATION: A1AT_variant_P357N_S359T

<400> SEQUENCE: 29

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190
```

```
Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
            340                 345                 350

Leu Glu Ala Ile Asn Met Thr Ile Pro Pro Glu Val Lys Phe Asn Lys
        355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys
385                 390

<210> SEQ ID NO 30
<211> LENGTH: 394
<212> TYPE: PRT
<213> ORGANISM: Artificial Sequence
<220> FEATURE:
<223> OTHER INFORMATION: A1AT_variant_P357N_C232S

<400> SEQUENCE: 30

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
            85                  90                  95

Gln Glu Leu Leu Arg Thr Leu Asn Gln Pro Asp Ser Gln Leu Gln Leu
        100                 105                 110

Thr Thr Gly Asn Gly Leu Phe Leu Ser Glu Gly Leu Lys Leu Val Asp
    115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160
```

```
Val Glu Lys Gly Thr Gln Gly Lys Ile Val Asp Leu Val Lys Glu Leu
            165                 170                 175

Asp Arg Asp Thr Val Phe Ala Leu Val Asn Tyr Ile Phe Lys Gly
        180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
210                 215                 220

Gly Met Phe Asn Ile Gln His Ser Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Asn Met Ser Ile Pro Pro Glu Val Lys Phe Asn Lys
        355                 360                 365

Pro Phe Val Phe Leu Met Ile Asp Gln Asn Thr Lys Ser Pro Leu Phe
        370                 375                 380

Met Gly Lys Val Val Asn Pro Thr Gln Lys
385                 390

<210> SEQ ID NO 31
<211> LENGTH: 394
<212> TYPE: PRT
<213> ORGANISM: Artificial Sequence
<220> FEATURE:
<223> OTHER INFORMATION: A1AT_variant_P357N_S359T_C232S

<400> SEQUENCE: 31

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125
```

Lys Phe Leu Glu Asp Val Lys Leu Tyr His Ser Glu Ala Phe Thr
            130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Ser Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Asn Met Thr Ile Pro Pro Glu Val Lys Phe Asn Lys
        355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys
385                 390

<210> SEQ ID NO 32
<211> LENGTH: 394
<212> TYPE: PRT
<213> ORGANISM: Artificial Sequence
<220> FEATURE:
<223> OTHER INFORMATION: A1AT-WildType

<400> SEQUENCE: 32

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

```
Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
            115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
            210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys
385                 390
```